(12) United States Patent
Harayama et al.

(10) Patent No.: US 7,994,339 B2
(45) Date of Patent: Aug. 9, 2011

(54) PHTHALAMIDE DERIVATIVE, AGRICULTURAL OR HORTICULTURAL PESTICIDE, AND USE OF THE PESTICIDE

(75) Inventors: Hiroto Harayama, Kawachinagano (JP); Masanori Tohnishi, Kawachinagano (JP); Shinsuke Fujioka, Kawachinagano (JP); Akiyuki Suwa, Kawachinagano (JP)

(73) Assignee: Nihon Nohyaku Co., Ltd., Tokyo (JP)

( * ) Notice: Subject to any disclaimer, the term of this patent is extended or adjusted under 35 U.S.C. 154(b) by 232 days.

(21) Appl. No.: 12/086,433

(22) PCT Filed: Dec. 14, 2006

(86) PCT No.: PCT/JP2006/324936
§ 371 (c)(1), (2), (4) Date: Jun. 12, 2008

(87) PCT Pub. No.: WO2007/069684
PCT Pub. Date: Jun. 21, 2007

(65) Prior Publication Data
US 2009/0111861 A1    Apr. 30, 2009

(30) Foreign Application Priority Data
Dec. 15, 2005   (JP) ................................. 2005-362037

(51) Int. Cl.
*C07D 257/04*      (2006.01)
(52) U.S. Cl. ..................................... 548/253
(58) Field of Classification Search ........................ None
See application file for complete search history.

(56) References Cited

U.S. PATENT DOCUMENTS

| | | | |
|---|---|---|---|
| 3,838,126 A | 9/1974 | Wagner et al. | |
| 4,746,353 A | 5/1988 | Levitt | |
| 6,603,044 B1 * | 8/2003 | Tohnishi et al. | 564/154 |
| 2002/0035266 A1 | 3/2002 | Sidduri | |
| 2003/0187043 A1 * | 10/2003 | Maurer et al. | 514/381 |
| 2004/0053786 A1 * | 3/2004 | Selby et al. | 504/249 |
| 2004/0082616 A1 | 4/2004 | Duncia et al. | |

FOREIGN PATENT DOCUMENTS

| | | | |
|---|---|---|---|
| EP | 0919542 | A2 | 6/1999 |
| EP | 1006107 | A2 | 6/2000 |
| GB | 787582 | A | 12/1957 |
| WO | WO 01/85705 | A1 | 11/2001 |
| WO | WO 02/32856 | A2 | 4/2002 |
| WO | WO2004/080984 | A1 | 9/2004 |

OTHER PUBLICATIONS

Curran-Everett et al. J. Appl. Physiol., 97:457-459, 2004.*
Chen et al., J. Pharmaceutical and Biomedical Analysis, 17 (1998), pp. 631-640.*
Golomolzin, B.V. et al. "Covalent hydration in thetetrazolol, . . . 5-cquinazoline hydration products" Khimiya Geterotsiklicheskikh Soedinenii, 1971, vol. 7, No. 1, p. 133-6.
Chem Abstract No. 47-47782, 1953, V. 47, 8067a-d: Wu, D. et al. "Substitute phenyltetrazoles . . . alkoxyaminophenyltetrazoles", J. Organic Chem., 1952, V. 17, p. 1216-27.
Chem Abstract No. 47:12159, 1953, V. 47, 2170g-I, 2171 a-h: Herbst, R. et al. "The synthesis of nitro-andaminophenvltetrazoles" J Organic Chem. 1952 V. 17 p. 262-71.
Chem Abstract No. 44:20715, 1950, V. 44, 4131a-e: Schueler, F. et al., "Absorption spectra and . . . aderivatives" J. Pharm and Exper. Therapeutics. 1949 V 97 p. 266-75.
Chem Abstract No. 43:8834, 1949, V. 43, 1865b-e: Gross, E. et al. "Tetrazole derivatives . . . aminophenyltetrazoles" J. Pharm and Exoer Therapeutics 1948. V. 92, p. 330-5.

\* cited by examiner

*Primary Examiner* — Rebecca Anderson
*Assistant Examiner* — Alicia L Otton
(74) *Attorney, Agent, or Firm* — Paul E. White, Jr.; Manelli Denison & Selter PLLC

(57) ABSTRACT

Disclosed is a phthalamide derivative represented by the general formula (I) or a salt thereof, which shows an excellent controlling effect for use as an agricultural or horticultural insecticide alone or in combination with other agricultural or horticultural insecticide, acaricide, nematicide, fungicide, herbicide, plant growth regulator, biopesticide or the like.

[Chemical structure] (I)

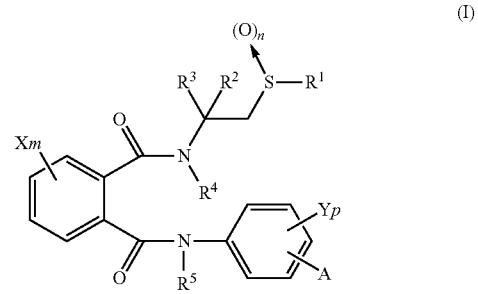

3 Claims, No Drawings

PHTHALAMIDE DERIVATIVE, AGRICULTURAL OR HORTICULTURAL PESTICIDE, AND USE OF THE PESTICIDE

This application is the national phase of international application PCT/JP2006/324936 filed 4 Dec. 2006 which designated the U.S.

TECHNICAL FIELD

The present invention relates to a phthalamide derivative, an agricultural or horticultural insecticide comprising the compound as an active ingredient and the use thereof.

BACKGROUND ART

It has been conventionally known that a certain phthalamide derivative is useful as an agricultural or horticultural insecticide (For example, refer to Patent Document 1). Furthermore, it is known that a phthalamide derivative having a similar structure to that of the present invention is useful as an agricultural or horticultural insecticide (For example, refer to Patent Document 2). However, the compound of the present invention having a tetrazolyl group in the structure thereof has been neither described nor suggested.
Patent Document 1: JP-A-11-240857
Patent Document 2: JP-A-2001-131141

DISCLOSURE OF THE INVENTION

Damage by harmful insects is still large in the production of crops in agriculture, horticulture and so on, and development of new agricultural or horticultural insecticides is demanded in view of factors such as emergence of harmful insects resistive to existing insecticides. In addition, various kinds of methods to save labor of insecticide application is demanded in consideration of aging of agricultural laborers, and creation of agricultural or horticultural insecticides having properties suitable for such insecticide application methods is demanded.

The present inventors have conducted intensive studies in order to develop a novel agricultural or horticultural insecticide, and consequently have found that phthalamide derivatives of the present invention represented by general formula (I) or the salts thereof are novel compounds not described in any documents and exhibit an excellent insecticidal effect at a low dosage as compared with the compounds described in the above-mentioned documents and that they can be excellent agricultural or horticultural insecticides which exhibit high absorption and migration properties from the root particularly when used for treatment of the soil, and thus they have completed the present invention.

That is, the present invention relates to a phthalamide derivative represented by general formula (I):

[Formula 1]

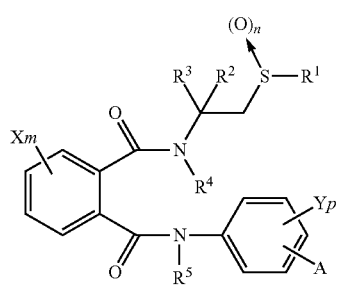

(I)

wherein $R^1$ represents a $C_1$-$C_6$ alkyl group, a halo $C_1$-$C_6$ alkyl group, a $C_2$-$C_6$ alkenyl group, a halo $C_2$-$C_6$ alkenyl group, a $C_2$-$C_6$ alkynyl group or a halo $C_2$-$C_6$ alkynyl group;
$R^2$ and $R^3$ may be the same or different, and each represents a hydrogen atom, a $C_1$-$C_6$ alkyl group, a halo $C_1$-$C_6$ alkyl group, a $C_2$-$C_6$ alkenyl group, a halo $C_2$-$C_6$ alkenyl group, a $C_2$-$C_6$ alkynyl group or a halo $C_2$-$C_6$ alkynyl group;
$R^4$ and $R^5$ may be the same or different, and each represents a hydrogen atom, a $C_1$-$C_6$ alkyl group, a $C_2$-$C_6$ alkenyl group, a $C_2$-$C_6$ alkynyl group, a $C_1$-$C_6$ alkylcarbonyl group, a halo $C_1$-$C_6$ alkylcarbonyl group, a $C_1$-$C_6$ alkoxycarbonyl group or a halo $C_1$-$C_6$ alkoxycarbonyl group;
A represents a tetrazolyl group represented by A-1

[Formula 2]

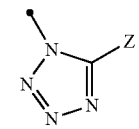

(A-1)

wherein Z represents a hydrogen atom, a $C_1$-$C_6$ alkyl group, a halo $C_1$-$C_{10}$ alkyl group, a $C_2$-$C_6$ alkenyl group, a halo $C_2$-$C_6$ alkenyl group, a $C_2$-$C_6$ alkynyl group, a halo $C_2$-$C_6$ alkynyl group, a $C_3$-$C_6$ cycloalkyl group, a halo $C_3$-$C_6$ cycloalkyl group, a phenyl group, a substituted phenyl group having one or more substituent groups, which may be the same or different, selected from a halogen atom, a cyano group, a nitro group, a $C_1$-$C_6$ alkyl group, a halo $C_1$-$C_6$ alkyl group, a $C_1$-$C_6$ alkoxy group and a halo $C_1$-$C_6$ alkoxy group, a heterocyclic group or a substituted heterocyclic group having one or more substituent groups, which may be the same or different, selected from a halogen atom, a cyano group, a nitro group, a $C_1$-$C_6$ alkyl group, a halo $C_1$-$C_6$ alkyl group, a $C_1$-$C_6$ alkoxy group and a halo $C_1$-$C_6$ alkoxy group;
or A-2

[Formula 3]

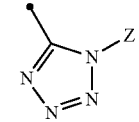

(A-2)

wherein Z is the same as above;
X represents a halogen atom, a nitro group, a cyano group, a $C_1$-$C_6$ alkyl group, a halo $C_1$-$C_6$ alkyl group, a $C_1$-$C_6$ alkoxy group, a halo $C_1$-$C_6$ alkoxy group, a $C_1$-$C_6$ alkylthio group, a halo $C_1$-$C_6$ alkylthio group, a $C_1$-$C_6$ alkylsulfinyl group, a halo $C_1$-$C_6$ alkylsulfinyl group, a $C_1$-$C_6$ alkylsulfonyl group or a halo $C_1$-$C_6$ alkylsulfonyl group, and m represents an integer of from 0 to 4;
Y represents a halogen atom, a nitro group, a cyano group, a $C_1$-$C_6$ alkyl group, a halo $C_1$-$C_6$ alkyl group, a $C_1$-$C_6$ alkoxy group, a halo $C_1$-$C_6$ alkoxy group, a $C_1$-$C_6$ alkylthio group, a halo $C_1$-$C_6$ alkylthio group, a $C_1$-$C_6$ alkylsulfinyl group, a halo $C_1$-$C_6$ alkylsulfinyl group, a $C_1$-$C_6$ alkylsulfonyl group or a halo $C_1$-$C_6$ alkylsulfonyl group, and p represents an integer of from 0 to 4;
n represents an integer of from 0 to 2; or a salt thereof, an agricultural or horticultural insecticide comprising the same as an active ingredient and the use thereof.

In addition, the present invention relates to an aniline derivative, which is an intermediate thereof, represented by general formula (III)

[Formula 4]

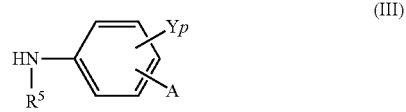

wherein $R^5$ represents a hydrogen atom, a $C_1$-$C_6$ alkyl group, a $C_2$-$C_6$ alkenyl group, a $C_2$-$C_6$ alkynyl group, a $C_1$-$C_6$ alkylcarbonyl group, a halo $C_1$-$C_6$ alkylcarbonyl group, a $C_1$-$C_6$ alkoxycarbonyl group or a halo $C_1$-$C_6$ alkoxycarbonyl group; A represents a tetrazolyl group represented by A-1

[Formula 5]

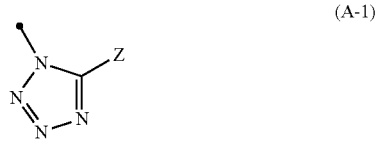

wherein Z represents a hydrogen atom, a $C_1$-$C_6$ alkyl group, a halo $C_1$-$C_{10}$ alkyl group, a $C_2$-$C_6$ alkenyl group, a halo $C_2$-$C_6$ alkenyl group, a $C_2$-$C_6$ alkynyl group, a halo $C_2$-$C_6$ alkynyl group, a $C_3$-$C_6$ cycloalkyl group, a halo $C_3$-$C_6$ cycloalkyl group, a phenyl group, a substituted phenyl group having one or more substituent groups, which may be the same or different, selected from a halogen atom, a cyano group, a nitro group, a $C_1$-$C_6$ alkyl group, a halo $C_1$-$C_6$ alkyl group, a $C_1$-$C_6$ alkoxy group and a halo $C_1$-$C_6$ alkoxy group, a heterocyclic group or a substituted heterocyclic group having one or more substituent groups, which may be the same or different, selected from a halogen atom, a cyano group, a nitro group, a $C_1$-$C_6$ alkyl group, a halo $C_1$-$C_6$ alkyl group, a $C_1$-$C_6$ alkoxy group and a halo $C_1$-$C_6$ alkoxy group;
or A-2

[Formula 6]

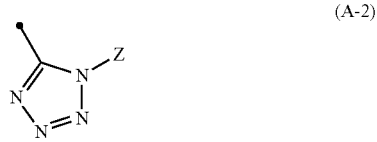

wherein Z is the same as above;
Y represents a halogen atom, a nitro group, a cyano group, a $C_1$-$C_6$ alkyl group, a halo $C_1$-$C_6$ alkyl group, a $C_1$-$C_6$ alkoxy group, a halo $C_1$-$C_6$ alkoxy group, a $C_1$-$C_6$ alkylthio group, a halo $C_1$-$C_6$ alkylthio group, a $C_1$-$C_6$ alkylsulfinyl group, a halo $C_1$-$C_6$ alkylsulfinyl group, a $C_1$-$C_6$ alkylsulfonyl group or a halo $C_1$-$C_6$ alkylsulfonyl group, and p represents an integer of from 0 to 4; or a salt thereof.

The phthalamide derivative of the present invention represented by general formula (I) exhibits an excellent preventive effect as an agricultural or horticultural insecticide and also achieves an excellent preventive effect when used in combination with another agricultural or horticultural insecticide, an acaricide, a nematocide, a fungicide, a herbicide, a plant-growth regulator, a biological agrochemical and the like.

BEST MODE FOR CARRYING OUT THE INVENTION

In the definition of general formula (I) of the phthalamide derivatives of the present invention, "a halogen atom" refers to a chlorine atom, a bromine atom, an iodine atom or a fluorine atom. A "$C_1$-$C_6$ alkyl group" refers to a linear or branched alkyl group having 1 to 6 carbon atoms and examples thereof include a methyl group, an ethyl group, an n-propyl group, an i-propyl group, an n-butyl, an i-butyl, an s-butyl, a t-butyl, an n-pentyl group, a neopentyl group, an n-hexyl group. A "halo $C_1$-$C_{10}$ alkyl group" refers to a linear or branched alkyl group having 1 to 10 carbon atoms and substituted by one or more halogen atoms, which may be the same or different, and examples thereof include a trifluoromethyl group, a difluoromethyl group, a perfluoroethyl group, a 1,2,2,2-tetrafluoro-1-(trifluoromethyl)ethyl group, a 2,2,2-trifluoro-1-(trifluoromethyl)ethyl group, a 2,2,2-trifluoro-1-methyl-1-(trifluoromethyl)ethyl group, a chloromethyl group, a bromomethyl group, a 1-bromoethyl group, a 2,3-dibromopropyl group. A "$C_1$-$C_6$ alkoxy group" refers to a linear or branched alkoxy group having 1 to 6 carbon atoms and examples thereof include a methoxy group, an ethoxy group, an n-propoxy group, an i-propoxy group, an n-butoxy group, an s-butoxy group, a t-butoxy group, an n-pentyl oxy group, an i-pentyl oxy group, a neopentyl oxy group, an n-hexyl oxy group. A "halo $C_1$-$C_6$ alkoxy group" refers to a linear or branched alkoxy group having 1 to 6 carbon atoms and substituted by one or more halogen atoms, which may be the same or different, and examples thereof include a difluoromethoxy group, a trifluoromethoxy group, a 2,2,2-trifluoroethoxy group.

As for "heterocyclic group", for example, a pyridyl group, a pyridine-N-oxide group, a pyrimidinyl group, a furyl group, a tetrahydrofuryl group, a thienyl group, a tetrahydrothienyl group, a tetrahydropyranyl group, a tetrahydrothiopyranyl group, an oxazolyl group, an isoxazolyl group, an oxadiazolyl group, a thiazolyl group, an isothiazolyl group, a thiadiazolyl group, an imidazolyl group, a triazolyl group, a pyrazolyl group, etc. can be exemplified and, as for "condensed ring", for example, naphthalene, tetrahydronaphthalene, indene, indane, quinoline, quinazoline, indole, indoline, chromane, isochromane, benzodioxane, benzodioxole, benzofuran, dihydrobenzofuran, benzothiophene, dihydrobenzothiophene, benzoxazole, benzothiazole, benzimidazole, indazole, etc. can be exemplified.

As for the salts of phthalamide derivatives of the present invention represented by general formula (I), for example, inorganic acid salts such as hydrochloric acid salts, sulfuric acid salts, nitric acid salts, phosphoric acid salts, organic acid salts such as acetic acid salts, fumaric acid salts, maleic acid salts, oxalic acid salts, methanesulfonic acid salts, benzenesulfonic acid salts, p-toluenesulfonic acid salts, and salts with a sodium ion, a potassium ion, a calcium ion, etc. can be exemplified. In addition, as for the salts of aniline derivatives represented by general formula (III) which are intermediates, for example, inorganic acid salts such as hydrochloric acid salts, sulfuric acid salts, nitric acid salts, phosphoric acid salts, organic acid salts such as acetic acid salts, fumaric acid salts, maleic acid salts, oxalic acid salts, methanesulfonic acid salts, benzenesulfonic acid salts, p-toluenesulfonic acid salts can be exemplified.

$R^1$ is preferably a $C_1$-$C_6$ alkyl group, and particularly preferably a methyl group or an ethyl group in phthalamide derivatives of the present invention represented by general formula (I). A hydrogen atom or a methyl group is particularly preferable as $R^2$ and $R^3$. A hydrogen atom is particularly preferable as $R^4$ and $R^5$. X is preferably a halogen atom, and particularly preferably a chlorine atom, a bromine atom or an iodine atom. m is preferably 1 or 2, and particularly preferably 1. Y is preferably a halogen atom, a $C_1$-$C_6$ alkyl group or a halo $C_1$-$C_6$ alkyl group, and particularly preferably it is a methyl group or a chlorine atom. p is preferably 1 or 2, and particularly preferably 1. Z is preferably a $C_1$-$C_6$ alkyl group, a halo $C_1$-$C_{10}$ alkyl group, a $C_2$-$C_6$ alkenyl group, a halo $C_2$-$C_6$ alkenyl group, a $C_2$-$C_6$ alkynyl group, a halo $C_2$-$C_6$ alkynyl group, a $C_3$-$C_6$ cycloalkyl group, a halo $C_3$-$C_6$ cycloalkyl group, a phenyl group, a substituted phenyl having one or more substituent groups, which may be the same or different, selected from a halogen atom, a cyano group, a nitro group, a $C_1$-$C_6$ alkyl group, a halo $C_1$-$C_6$ alkyl group, a $C_1$-$C_6$ alkoxy group and a halo $C_1$-$C_6$ alkoxy group or a heterocyclic group, and particularly preferably it is a halo $C_1$-$C_{10}$ alkyl group. As for n, any integer from 0 to 2 is preferable but 2 is particularly preferable.

There are cases that the phthalamide derivative of the present invention represented by general formula (I) has one or more asymmetric carbon atoms or asymmetric centers in the structural formula, and there are also cases that there exist two or more optical isomers and diastereomer, and the present invention includes each of these optical isomers as well as any mixture in which the isomers are contained in an arbitrary ratio. In addition, there are cases that there are two or more geometrical isomers due to one or more carbon-carbon double bonds in the structural formula of the sulfonamide derivatives of the present invention represented by general formula (I), and the present invention includes each of these geometrical isomers as well as any mixture in which the isomers are contained in an arbitrary ratio.

The phthalamide derivatives of the present invention represented by general formula (I) can be produced following the process described in JP-A-11-240857 or JP-A-2001-131141 and, for example, by the production processes illustrated bellow, but the production process is not limited to these.
Production Process 1.

wherein $R^1$, $R^2$, $R^3$, $R^4$, $R^5$, A, X, Y, Z, m, n and p are the same as above, and hal represents a halogen atom.)

A phthalisoimide derivative represented by general formula (II) and an aniline derivative represented by general formula (III) are reacted in an inert solvent in the presence or absence of an acid or a base to obtain a phthalamide derivative represented by general formula (I-1). The phthalamide derivative (I-1) is reacted with a halide represented by general formula (IV) in the presence of a dehydrohalogenating agent and an inert solvent to obtain a phthalamide derivative represented by general formula (I-2). The phthalamide derivative represented by general formula (I) can be produced by reacting the phthalamide derivative represented by general formula (I-2) with an oxidizing agent in the presence of an inert solvent. When $R^4$ is a hydrogen atom, the phthalamide derivative represented by general formula (I) can be produced by reacting the phthalamide derivative represented by general formula (I-1) with an oxidizing agent in the presence of an inert solvent without going through the phthalamide derivative represented by general formula (I-2).

[1-1] General Formula (II)→General Formula (I-1)

This reaction can be conducted according to the process described in J. Med. Chem., 1967, vol. 10, p. 982 to produce an desired compound. As for the inert solvent to be used in this reaction, any solvent which does not significantly inhibit progress of this reaction and examples thereof include linear or cyclic ethers such as tetrahydrofuran, diethyl ether, methyl t-butyl ether, dioxane, halogenated hydrocarbons such as chloroform, methylene chloride, halogenated aromatic hydrocarbons such as chlorobenzene, dichlorobenzene, aromatic hydrocarbons such as toluene, xylene, nitriles such as acetonitrile, esters such as ethyl acetate, butyl acetate and these inert solvents can be used singly or as a mixture of two or more of them. As for the acid usable in this reaction, for example, organic acids such as acetic acid, trifluoroacetic acid, inorganic acids such as hydrochloric acid, sulfuric acid can be exemplified, and an amount to be used can be appropriately selected from a range from a catalytic amount to an

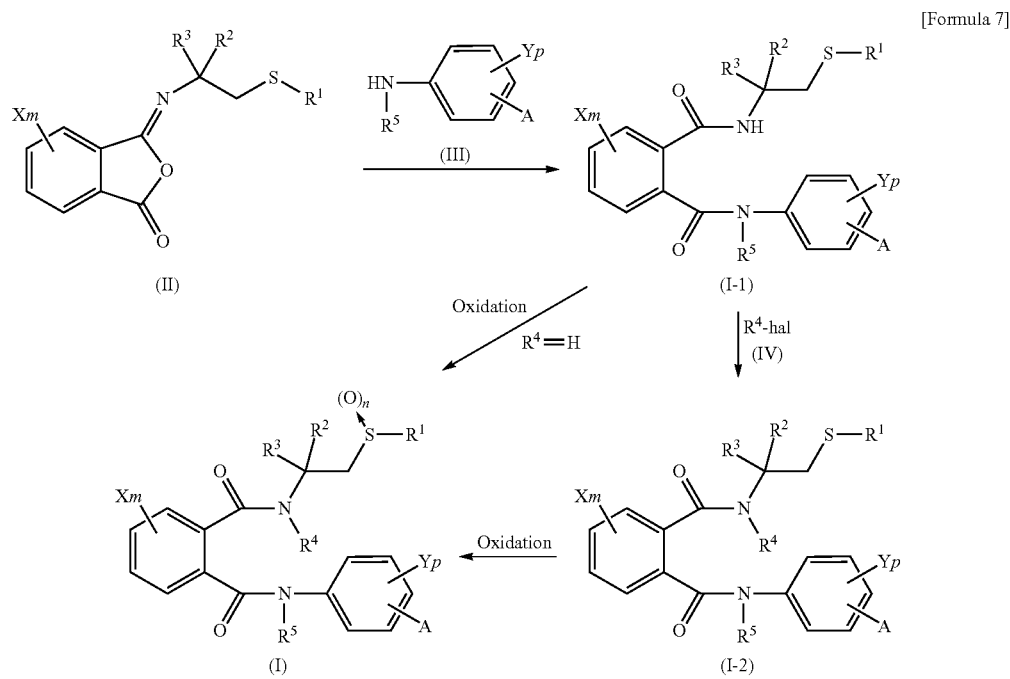

[Formula 7]

excess molar amount for the phthalisoimide derivative represented by general formula (II) and used. As for the base, for example, organic bases such as triethylamine, pyridine, inorganic bases such as potassium carbonate, sodium hydrogen carbonate, sodium carbonate, sodium hydroxide can be exemplified, and an amount to be used can be appropriately selected from a range from a catalytic amount to an excess molar amount for the phthalisoimide derivative represented by general formula (II) and used. The reaction can be performed at temperatures within a range from 0° C. to a boiling point of the inert solvent used, and the reaction time is in a range from several minutes to 48 hours although it may vary depending on reaction scale and reaction temperature. After the reaction ends, the desired compound can be isolated from the reaction system containing the desired compound by an ordinary method and can be purified by recrystallization, column chromatography and so on as required to produce the desired compound.

[1-2] General Formula (I-1)→General Formula (I-2)

As for the inert solvent to be used in this reaction, any solvent which does not significantly inhibit progress of this reaction and examples thereof include aromatic hydrocarbons such as benzene, toluene, xylene, halogenated aromatic hydrocarbons such as fluorobenzene, chlorobenzene, dichlorobenzene, halogenated hydrocarbons such as methylene chloride, chloroform, carbon tetrachloride, linear or cyclic ethers such as diethyl ether, dioxane, tetrahydrofuran, esters such as ethyl acetate, amides such as dimethylformamide, dimethylacetamide, acids such as acetic acid, dimethylsulfoxide, 1,3-dimethyl-2-imidazolidinone and these inert solvents can be used singly or as a mixture of two or more of them. As for the dehydrohalogenating agent, for example, organic bases such as triethylamine, pyridine, inorganic bases such as potassium carbonate, sodium hydrogen carbonate, sodium carbonate, sodium hydroxide can be exemplified. Since this reaction is an equimolar reaction, each of the reactants can be used in a molar equivalent amount but any of the reactants can be excessively used as well. The reaction can be performed at temperatures within a range from room temperature to a reflux temperature of the inert solvent used, and the reaction time can be selected from a range from several minutes to 48 hours although it may vary depending on reaction scale and reaction temperature. After the reaction ends, the desired compound can be isolated from the reaction system containing the desired compound by an ordinary method and can be purified by recrystallization, column chromatography and so on as required to produce the desired compound. The desired compound can also be used at the next reaction step without being isolated from reaction system.

[1-3] General Formula (I-1) or (I-2)→General Formula (I)

As for the inert solvent to be used in this reaction, any solvent which does not significantly inhibit progress of this reaction and examples thereof include halogenated hydrocarbons such as methylene chloride, chloroform, aromatic hydrocarbons such as toluene, xylene, halogenated aromatic hydrocarbons such as fluorobenzene, chlorobenzene, dichlorobenzene, acids such as acetic acid, and alcohols such as methanol, ethanol, propanol. As for the oxidizing agent, for example, m-chloroperbenzoic acid, peracetic acid, potassium metaperiodate, hydrogen persulfate potassium (oxone), hydrogen peroxide can be exemplified and the amount to be used can be appropriately selected from a range from 0.5 to 3 molar equivalents for the phthalamide derivative represented by general formula (I-1) or (I-2) and used. The reaction can be performed at temperatures within a range from −50° C. to a boiling point of an inert solvent used, and the reaction time is in a range from several minutes to 24 hours although it may vary depending on reaction temperature and reaction scale. After the reaction ends, the desired compound can be isolated from the reaction system containing the desired compound by an ordinary method and can be purified by recrystallization, column chromatography and so on as required to produce the desired compound.

The phthalisoimide derivatives represented by general formula (II) which are starting material compounds of the present invention can be produced following the production processes described in JP-A-11-240857 and JP-A-2001-131141.

The aniline derivatives represented by general formula (III) which are starting material compounds of the present invention can be produced by combining the production processes described in J. Org. Chem., 1976, vol. 41, p. 1073 or J. Org. Chem., 1993, vol. 58, p. 32 and, for example, can be produced by a production process to illustrate as follows.

Production Process 2.

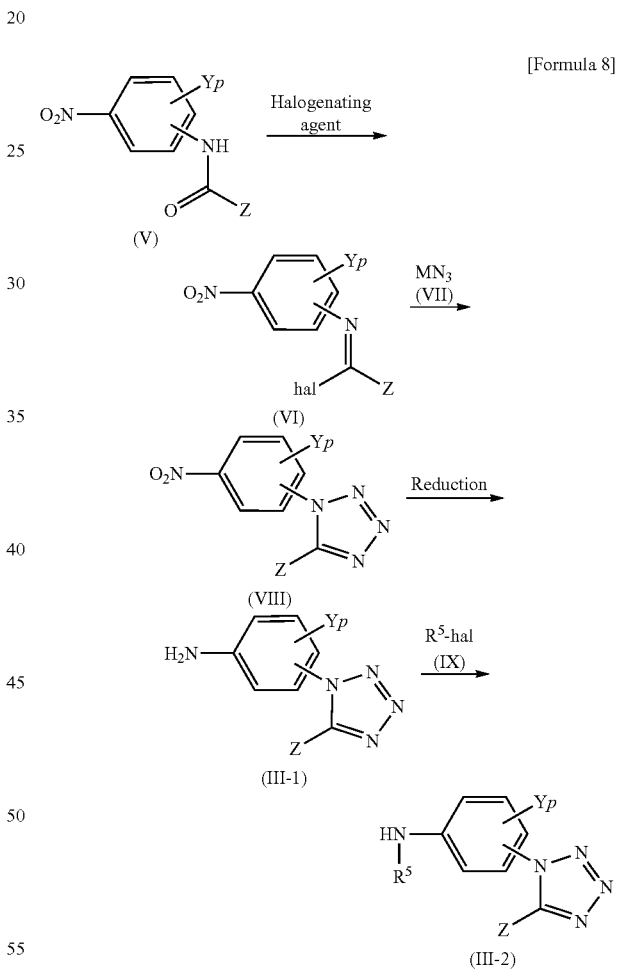

[Formula 8]

wherein $R^5$, Y, Z, p and hal are the same as above, and M represents a metal atom such as a sodium atom, a potassium atom or a trimethylsilyl group.)

An anilide derivative represented by general formula (V) and a halogenating agent are reacted in the presence an inert solvent to obtain a haloimide derivative represented by general formula (VI). The haloimide derivative (VI) is, after isolated or not isolated, reacted with an azide represented by general formula (VII) in the presence of an inert solvent to obtain a tetrazole derivative represented by general formula (VIII). The aniline derivative of the present invention represented by general formula (III-1) can be produced by reducing the tetrazole derivative represented by general formula (VIII), after isolated or not isolated, in the presence of an inert solvent. In addition, the aniline derivative of the present invention represented by general formula (III-2) can be produced by reacting the aniline derivative of the present invention represented by general formula (III-1) with a halide represented by general formula (IX) in the presence of a base and an inert solvent.

[2-1] General Formula (V)→General Formula (VI)

As for the inert solvent to be used in this reaction, any solvent which does not significantly inhibit progress of this reaction and examples thereof include halogenated hydrocarbons such as methylene chloride, chloroform, aromatic hydrocarbons such as toluene, xylene, nitriles such as acetonitrile, halogenated aromatic hydrocarbons such as fluorobenzene, chlorobenzene, dichlorobenzene and these inert solvents can be used singly or as a mixture of two or more of them. As for the halogenating agent, for example, thionyl chloride, thionyl bromide, phosphorus trichloride, phosphorous pentachloride, phosphorus oxychloride, phosphorus tribromide, phosphorus oxybromide, carbon tetrachloride-triphenylphosphine, carbon tetrabromide-triphenylphosphine can be exemplified and the amount to be used can be appropriately selected from a range from 0.5 to 3 molar equivalents for the anilide derivative represented by general formula (V) and used. The reaction can be performed at temperatures within a range from −50° C. to the boiling point of the inert solvent used, and the reaction time is in a range from several minutes to 24 hours although it may vary depending on reaction temperature and reaction scale. After the reaction ends, the desired compound can be isolated from the reaction system containing the desired compound by an ordinary method and can be purified by recrystallization, column chromatography and so on as required to produce the desired compound. The desired compound can also be used at the next reaction step without being isolated from reaction system.

[2-2] General Formula (VI)→General Formula (VIII)

As for the inert solvent to be used in this reaction, any solvent which does not significantly inhibit progress of this reaction and examples thereof include halogenated hydrocarbons such as methylene chloride, chloroform, aromatic hydrocarbons such as toluene, xylene, halogenated aromatic hydrocarbons such as fluorobenzene, chlorobenzene, dichlorobenzene, amides such as dimethylformamide, dimethylacetamide, nitriles such as acetonitrile, dimethylsulfoxide, 1,3-dimethyl-2-imidazolidinone and these inert solvents can be used singly or as a mixture of two or more of them. As for the azide usable in this reaction, for example, sodium azide, potassium azide, trimethylsilyl azide can be exemplified and an amount to be used can be appropriately selected from a range from 0.5 to 3 molar equivalents for the haloimide derivative represented by general formula (VI) and used. The reaction can be performed at temperatures within a range from −50° C. to the boiling point of the inert solvent used, and the reaction time is in a range from several minutes to 24 hours although it may vary depending on reaction scale and reaction temperature. After the reaction ends, the desired compound can be isolated from the reaction system containing the desired compound by an ordinary method and can be purified by recrystallization, column chromatography and so on as required to produce the desired compound. The desired compound can also be used at the next reaction step without being isolated from reaction system.

[2-3] General Formula (VIII)→General Formula (III-1)

As for the inert solvent to be used in this reaction, any solvent which does not significantly inhibit progress of this reaction and examples thereof include alcohols such as methanol, ethanol, ethers such as tetrahydrofuran, dioxane, water and these inert solvents can be used singly or as a mixture of two or more of them. An aqueous solution of an acid used as a reducing agent shown below can be also used as an inert solvent as it is. As for the reducing agent usable in this reaction, metal-acid, metal-salt and so on can be exemplified, and examples of the metal include iron, tin, zinc, examples of the acid include inorganic acids such as hydrochloric acid, sulfuric acid, organic acids such as acetic acid, examples of the salt include ammonium chloride and tin chloride. These can be also used in combination. The amount of the reducing agent to be used can be appropriately selected from a range from 1 to 10 mol of metal or 0.05 to 10 mol of acid/salt for the tetrazole derivative represented by general formula (VIII) and used. The reductive reaction can be also performed by catalytic hydrogenation in the presence of a catalyst. As for the catalyst, for example, palladium carbon and Raney nickel can be exemplified and, the amount of catalyst can be appropriately selected from a range from 0.00001 to 0.1 molar times of the tetrazole derivative represented by general formula (VIII). The hydrogen pressure can be appropriately selected from a range from normal pressure to 100 kg/cm$^2$ and preferable from a range from normal pressure to 10 kg/cm$^2$. The reaction temperature can be selected from a range from 0° C. to 150° C. and the reaction time can be appropriately selected from a range from several minutes to 48 hours although it may vary depending on reaction scale and reaction temperature. After the reaction ends, the desired compound can be isolated from the reaction system containing the desired compound by an ordinary method and can be purified by recrystallization, column chromatography and so on as required to produce the desired compound. The desired compound can also be used at the next reaction step without being isolated from reaction system.

[2-4] General Formula (III-1)→General Formula (III-2)

This reaction can be performed in the same way as in [1-2]. Production Process 3.

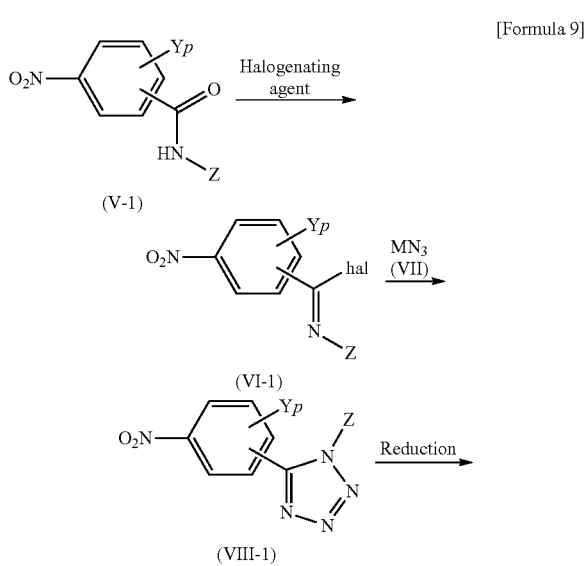

[Formula 9]

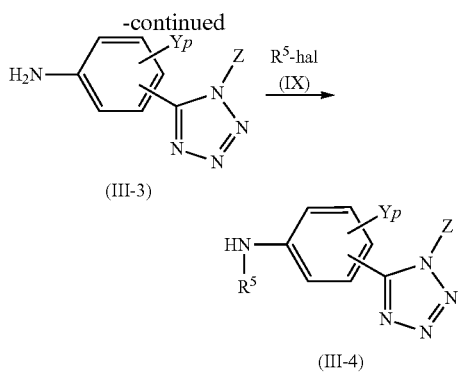

(III-3)

(III-4)

wherein R⁵, Y, Z, p, hal and M are the same as above.)

A benzamide derivative represented by general formula (V-1) and a halogenating agent are reacted in the presence of an inert solvent to obtain a haloimide derivative represented by general formula (VI-1). The haloimide derivative (VI-1) is, after isolated or not isolated, reacted with an azide represented by general formula (VII) in the presence of an inert solvent to obtain a tetrazole derivative represented by general formula (VIII-1). The aniline derivative of the present invention represented by general formula (III-3) can be produced by reducing the tetrazole derivative represented by general formula (VIII-1), after isolated or not isolated, in the presence of an inert solvent. In addition, the aniline derivative of the present invention represented by general formula (III-4) can be produced by reacting the aniline derivative of the present invention represented by general formula (III-3) with a halide represented by general formula (IX) in the presence of a base and an inert solvent.

[3-1] General Formula (V-1)→General Formula (VI-1)
This reaction can be performed in the same way as in [2-1].
[3-2] General Formula (VI-1)→General Formula (VIII-1)
This reaction can be performed in the same way as in [2-2].
[3-3] General Formula (VIII-1)→General Formula (III-3)
This reaction can be performed in the same way as in [2-3].
[3-4] General Formula (III-3)→General Formula (III-4)
This reaction can be performed in the same way as in [1-2].

The agricultural or horticultural insecticides, containing a phthalamide derivative represented by the formula (I) of the present invention as an active ingredient, are suitable for controlling various insect pests such as agricultural or horticultural insect pests, stored grain insect pests, sanitary insect pests, nematodes, etc., which are injurious to paddy rice, fruit trees, vegetables, other crops, flowers, ornamental plants, etc. They have a marked insecticidal effect, for example, on LEPIDOPTERA including summer fruit tortrix (*Adoxophyes orana fasciata*), smaller tea tortrix (*Adoxophyes* sp.), Manchurian fruit moth (*Grapholita inopinata*), oriental fruit moth (*Grapholita molesta*), soybean pod borer (*Leguminivora glycinivorella*), mulberry leafroller (*Olethreutes mori*), tea leafroller (*Caloptilia theivora*), *Caloptilia* sp. (*Caloptilia zachrysa*), apple leafminer (*Phyllonorycter ringoniella*), pear barkminer (*Spulerina astaurota*), common white (*Pieris rapae crucivora*), tobacco budworm (*Heliothis* sp.), codling moth (*Laspeyresia pomonella*), diamondback moth (*Plutella xylostella*), apple fruit moth (*Argyresthia conjugella*), peach fruit moth (*Carposina sasakii*), rice stem borer (*Chilo suppressalis*), rice leafroller (*Cnaphalocrocis medinalis*), tobacco moth (*Ephestia elutella*), mulberry pyralid (*Glyphodes pyloalis*), yellow rice borer (*Scirpophaga incertulas*), rice skipper (*Parnara guttata*), rice armyworm (*Mythimna separata*), pink borer (*Sesamia inferens*), common cutworm (*Spodoptera litura*), beet armyworm (*Spodoptera exigua*), etc.; HEMIPTERA including aster leafhopper (*Macrosteles fascifrons*), green rice leafhopper (*Nephotettix cincticeps*), brown rice planthopper (*Nilaparvata lugens*), whitebacked rice planthopper (*Sogatella furcifera*), citrus psylla (*Diaphorina citri*), grape whitefly (*Aleurolobus taonabae*), sweetpotato whitefly (*Bemisia tabaci*), greenhouse whitefly (*Trialeurodes vaporariorum*), turnip aphid (*Lipaphis erysimi*), green peach aphid (*Myzus persicae*), Indian wax scale (*Ceroplastes ceriferus*), cottony citrus scale (*Chloropulvinaria aurantii*), camphor scale (*Pseudaonidia duplex*), San Jose scale (*Diaspidiotus perniciosus*), arrowhead scale (*Unaspis yanonensis*), etc.; TYLENCHIDA including root-lesion nematode (*Pratylenchus* sp.), soybean beetle (*Anomala rufocuprea*), Japanese beetle (*Popillia japonica*), tobacco beetle (*Lasioderma serricorne*), powderpost beetle (*Lyctus brunneus*), twenty-eight-spotted ladybird (*Henosepilachna vigintioctopunctata*), adzuki bean weevil (*Callosobruchus chinensis*), vegetable weevil (*Listroderes costirostris*), maize weevil (*Sitophilus zeamais*), boll weevil (*Anthonomus grandis grandis*), rice water weevil (*Lissorhoptrus oryzophilus*), cucurbit leaf beetle (*Aulacophora femoralis*), rice leaf beetle (*Oulema oryzae*), striped flea beetle (*Phyllotreta striolata*), pine shoot beetle (*Tomicus piniperda*), Colorado potato beetle (*Leptinotarsa decemlineata*), Mexican bean beetle (*Epilachna varivestis*), corn rootworm (*Diabrotica* sp.), etc.; DIPTERA including melon fly (*Bactrocera cucurbitae*), oriental fruit fly (*Bactrocera dorsalis*), rice leafminer (*Agromyza oryzae*), onion maggot (*Delia antiqua*), seedcorn maggot (*Delia platura*), soybean pod gall midge (*Asphondylia yushimai*), house fly (*Musca domestica*), house mosquito (*Culex pipiens pallens*), etc.; TYLENCHIDA including coffee root-lesion nematode (*Pratylenchus coffeae*), potato cyst nematode (*Glabodera rostochiensis*), root-knot nematode (*Meloidogyne* sp.), citrus nematode (*Tylenchulus semipenetrans*), *Aphelenchus* sp. (*Aphelenchus avenae*), chrysanthemum foliar nematode (*Aphelenchoides ritzemabosi*), etc.; and ACARINA including citrus red mite (*Panonychus citri*), fruit tree red spider mite (*Panonychus ulmi*), carmine spider mite (*Tetranychus cinnabarinus*), Kanzawa spider mite (*Tetranychus Kanzawai* Kishida), two-spotted spider mite (*Tetranychus urticae* Koch), pink tea rust mite (*Acaphylla theavagrans*), pink citrus rust mite (*Aculops pelekassi*), purple tea mite (*Calacarus carinatus*), pear rust mite (*Epitrimerus pyri*), etc.

In addition, the present invention has a remarkable ant-killing effect on all kinds of termites, which damage houses, building materials, furniture, hides and leather, fibers, vinyl articles, electric wires/cables, such as of the Rhinotermitidae family including Formosan subterranean termite (*Coptotermes formosanus* Shiraki), reticulitermes (*Reticulitermes speratus* (Kolbe)), *Reticulitermes hesperus, Reticulitermes tibialis* and *Reticulitermes flavipes* inhabiting North America, *Reticulitermes lucifugus* and *Reticulitermes santonensis* inhabiting coast areas of the Mediterranean Sea, Western drywood termite (*Incisitermes minor* (Hagen)) and Taiwan white ant (*Odontotermes formosanus* (Shiraki)) of Termitidae family Daikoku white ant (*Cryptotermes domesticus* (Haviland)) of Kalotermitidae and *Hodotermopsis jzponica* (Holmgren) of the Termopsidae family at a low dosage. The present invention also has a remarkable ant-killing effect on ants, which invade crops or public facilities such as parks and houses and harm people, such as those of the Formicidae family including little black ant (*Monomorium pharaonis* Linnes), *Monomorium nipponense* Wheeler, Carpenter ant (*Camponotus kiusiuensis* Santschi), *Formica japonica* Motschulsky, *Lasius nipponensis* Forel) and fire ant (*Solenopsis richteri, Solenopsis invicta, Solenopsis geminata* (F)) inhabiting North America etc.

Furthermore, the phthalamide derivative of the present invention represented by general formula (I) can be used for external parasites of domestic animals such as cow, horse and sheep, pets such as dog and cat as well as rodents animals such as mouse, rat, hamster and squirrel, lagomorph animals, carnivora animals such as ferret, birds such as duck, cock and dove, and have a strong insecticide effect on external parasites such as Aphaniptera pests such as cat flea (*Ctenocephalides felis*), dog flea (*Ctenocephalides canis*) and *Xenopsylla cheopis*, Acarina pests such as *Haemaphyxalis longicornis* and *Boophilus microplus*, Anoplura pests such as cattle louse (*Haematopinus eurysternus*) and sheep louse (*Damalinia ovis*).

The agricultural or horticultural insecticide, which contains a phthalamide derivative represented by the formula (I) of the present invention as an active ingredient has a marked controlling effect on the above-exemplified insect pests, which are injurious to paddy field crops, upland crops, fruit trees, vegetables and other crops, flowers and ornament plants, and the like. Therefore, the desired effect of the agricultural or horticultural insecticide of the present invention can be exhibited by applying the insecticide to the nursery facility, seeds, paddy field water, stalks and leaves or soil of paddy field, upland field, fruit trees, vegetables, other crops or flowers and ornament plants at a season at which the insect pests are expected to appear, before their appearance or at the time when their appearance is confirmed. Particularly, a preferable application for using the agricultural or horticultural insecticide of the present invention is the application for which both of "penetration and translocation" are utilized, wherein the present agricultural or horticultural insecticide is applied to the nursery soil of crops, ornamental plants or the like; the planting hole soil at a transplantation; the plant foot; the irrigation water; or the cultural water of a water culture; so as to absorb the optically active phthalamide derivatives of the present invention from the roots through or not through the soil. Moreover, in recent years, IPM (integrated pest management) technology using genetically modified crops (herbicide-resistant crops, pest-resistant crops into which an insecticidal protein-generating gene has been incorporated, disease-resistant crops into which a gene generating a substance inducing resistance to disease has been incorporated, crops with improved taste, crops with improved keeping quality, crops with improved yield, etc.), insect pheromones (communication-disturbing agents used for Tortricidae or Mamestra, etc.), or natural enemy insects, has been developed. The agricultural or horticultural insecticide of the present invention can be used in admixture with such a technique, or can be used in systematization therewith.

Plants to which the agricultural or horticultural insecticide of the present invention can be applied are not particularly limited. Such plants include the following examples.

Examples of such plants may include cereals (e.g. rice, barley, wheat, rye, oat, corn, etc.), beans (soybeans, adzuki beans, horse beans, peas, red beans, peanuts, etc.), orchards/fruits (apples, citrus fruits, pomes, grapes, peaches, ume apricots, yellow peaches, walnuts, chestnuts, almonds, bananas, strawberries, etc.), leave/fruit crops (cabbage, tomato, spinach, broccoli, lettuce, onion, green onion, bell pepper, egg plant, pepper, etc.), root crops (carrot, potato, sweet potato, aroid, Japanese radish, lotus root, turnip, burdock, garlic, etc.), processed products (cotton, hemp, beet, hop, sugar cane, sugar beet, olive, gum, coffee, tobacco, tea, etc.), pepos (pumpkin, cucumber, *Cucumis melo*, watermelon, melon, etc.), pasture plants (orchard grass, sorgum, timothy, clover, alfalfa, etc.), turf grasses (lawn, bent grass, etc.), ornamental plants such as perfume (lavender, rosemary, thyme, parsley, pepper, ginger, etc.), flowering plants (chrysanthemum, rose, carnation, orchid, etc.), garden trees (ginkgo, cherry tree, Japanese laurel, etc.), and forest trees (*Abies sachalinensis, Picea jezoensis*, pine, thuja, Japanese cedar, Japanese cypress, etc.).

In order to control various types of insect pests, the agricultural or horticultural insecticide of the present invention is applied at an amount effective for controlling insect pests or nematodes, directly, or in the form of being diluted with water or the like, or in the form of being suspended in water or the like, to plants regarding which the infestation of such insect pests or nematodes is forecasted. When the present agricultural or horticultural insecticide is applied to orchards, cereals, vegetables, and the like, infested with insect pests or nematodes, for example, it is applied to leaves or stems thereof, or it can also be applied by treatments including: seed treatments such as immersion of seeds in the agent, or dust coating of seeds, or calper treatment; and soil treatments in which the soil is treated with the agent, so as to allow plants to absorb the agent from roots thereof, such as mixing of the agent into all layers of the soil, row treatment, mixing the agent into bed soil, cell nursery treatment, planting hole treatment, plant foot treatment, top dressing, rice box treatment, or submerged application. In addition, addition of the agent to the solution in solution (slop) culture, fumigation, or injection of the agent into tree trunks, may also be applied. Moreover, the agricultural or horticultural insecticide of the present invention may be applied at an amount effective for controlling insect pests or nematodes, directly, or in the form of being diluted with water or the like, or in the form of being suspended in water or the like, to plants regarding which the infestation of such insect pests or nematodes is forecasted. For example, the present agricultural or horticultural insecticide is applied to stored grain insect pests, house insect pests, sanitary insect pests, forest insect pests, or the like. Otherwise, it may also be used by methods such as application to house construction materials, fumigation, or baiting.

Examples of a seed treatment method may include: a method which comprises diluting or not diluting a liquid or solid formulation and then immersing seeds in the obtained solution, so as to allow an active ingredient to permeate into the seeds; a method which comprises mixing a solid or liquid formulation with seeds or dust-coating, so as to allow an active ingredient to attach onto the surface of the seeds; a method which comprises mixing an active ingredient with an adhesive carrier such as a resin or polymer and then coating seeds with the resultant product; and a method of applying the agent around seeds at the same time of planting.

The term "seed" that is subjected to the above seed treatments means a plant body that is at the initial stage of culture for the reproduction of plants. Examples of such a seed may include a seed, a bulb, a tuber, a seed tuber, a stock bud, a propagule, a bulblet, and a plant body used for vegetative reproduction in cutting culture.

The term "soil" or "culture carrier" for plants in the case of applying the use method of the present invention means a supporting medium for the culture of plants, and particularly, a supporting medium in which plant roots are allowed to extend. The material of the soil or culture carrier is not specifically limited, as long as plants can grow thereon. Thus, such a soil or culture carrier may be what is called soil, a raising planting mat, water, or the like. Examples of a specific material may include sand, pumice, vermiculite, diatomous earth, agar, a gelatinous substance, a polymer, a rock wool, a glass wool, a wood chip, and a bark.

Examples of a method of applying the agent to the stems or leaves of plants, stored grain insect pests, house insect pests, sanitary insect pests, forest insect pests, or the like, may include: a method which comprises diluting a liquid formulation such as an emulsion or flowable or a solid formulation such as a wettable powder or water dispersible granule with water, as appropriate, and then applying the obtained solution to the target; a method of applying a dust; and fumigation.

Examples of a method of applying the agent to the soil may include: a method which comprises diluting or not diluting a liquid formulation with water and then applying the obtained solution to the bottom portion of a plant body or a nursery bed for raising seedling; a method which comprises applying granules to the bottom portion of a plant body or a nursery bed for raising seedling; a method which comprises applying the agent that is in the form of a dust, a wettable powder, a water dispersible granule, granules, or the like, to the soil before sowing or transplantation, so as to mix the agent into the soil as a whole; and a method which comprises applying the agent that is in the form of a dust, a wettable powder, a water dispersible granule, granules, or the like, to planting holes or rows before sowing or planting of plant bodies.

With regard to a method of applying the agent to a nursery box used for paddy rice, a formulation may be different depending on the period of application of the agent, such as application during sowing, application during greening period, or application during transplantation. The agent may be applied in a formulation such as a dust, a water dispersible granule, or granules. The agent may also be applied by mixing it with molding. Mixing of the molding with a dust, a water dispersible granule, or granules, may be applied. For example, the agent may be mixed into seedbed soil, cover soil, or the molding as a whole. The agent may simply be applied by placing the molding and various types of formulations alternately in a layer form.

As a method of applying the agent to the paddy field, the agent that is in a solid formulation, such as a jumbo formulation, a pack formulation, granules, or a water dispersible granule, or the formulation that is in a liquid form, such as a flowable or an emulsion, is generally applied in the paddy field filled with water. In addition, during the rice planting period, the agent that is in an appropriate formulation may be applied to or injected into the soil, directly or after being mixed with fertilizer. Moreover, the agent that is in the form of an emulsion or a flowable is applied to the source of water supply to the paddy field, such as a waterspout or irrigation equipment, so as to apply the agent together with the supply of water in a labor-saving manner.

For field crops, the agent can be applied to seeds or a culture carrier that is adjacent to plant bodies, during the sowing and raising seedling periods. In the case of plants that are directly sown to the field, direct application of the agent to seeds, and application of the agent to the bottom portions of plants during culture, are preferable. In addition, a method of applying the agent that is in a granule form and a method of applying the agent that has been diluted or undiluted with water in a liquid state are also possible. A method which comprises mixing the agent that is in a granule form with a culture carrier before sowing and then sowing seeds on the carrier is also preferable.

As a method of applying the agent during the sowing and raising planting periods of culture plants to be transplanted, a method of directly applying the agent to seeds, a method of applying the agent that is in a liquid state to a nursery bed for raising planting, and a method of applying the agent that is in a granule form, are preferable. In addition, a method of applying the agent that is in a granule form into planting holes during fix planting, and a method of mixing the agent with a culture carrier around the place to which the plants to be transplanted, are also preferable.

The agricultural or horticultural insecticide of the present invention is generally prepared into suitable formulations according to a conventional manner for preparation of agrochemicals.

That is, the phthalamide derivative represented by the formula (I) and, optionally, an adjuvant are blended with a suitable inert carrier in a proper proportion and prepared into a suitable formulation such as a suspension, emulsion, solution, wettable powder, water dispersible granule, granule, dust, tablets, pack or the like through dissolution, dispersion, suspension, mixing, impregnation, adsorption or sticking.

The inert carrier usable in the present invention may be either solid or liquid. As a material usable as the solid carrier, there can be exemplified soybean flour, cereal flour, wood flour, bark flour, saw dust, powdered tobacco stalks, powdered walnut shells, bran, powdered cellulose, extraction residue of vegetables, synthetic polymers such as powdered synthetic resins, clays (e.g. kaolin, bentonite, and acid clay), talcs (e.g. talc and pyrophyllite), silica powders or flakes (e.g. diatomaceous earth, silica sand, mica and white carbon [synthetic high dispersion silicic acid, also called finely divided hydrated silica or hydrated silicic acid, some of commercially available products contain calcium silicate as the major component]), activated carbon, powdered sulfur, pumice, calcined diatomaceous earth, ground brick, fly ash, sand, calcium carbonate, calcium phosphate and other inorganic or mineral powders, plastic carriers such as polyethylene, polypropylene, polyvinylidene chloride and the like, chemical fertilizers (e.g. ammonium sulfate, ammonium phosphate, ammonium nitrate, urea and ammonium chloride), and compost. These carriers may be used alone or as a mixture thereof.

A material usable as the liquid carrier is selected from materials that have solubility in themselves or which are without such solubility but are capable of dispersing an active ingredient with the aid of an adjuvant. The following are typical examples of the liquid carrier and can be used alone or as a mixture thereof: water, alcohols (e.g. methanol, ethanol, isopropanol, butanol and ethylene glycol), ketones (e.g. acetone, methyl ethyl ketone, methyl isobutyl ketone, diisobutyl ketone and cyclohexanone), ethers (e.g. ethyl ether, dioxane, Cellosolve, dipropyl ether and tetrahydrofuran), aliphatic hydrocarbon (e.g. kerosene and mineral oils), aromatic hydrocarbons (e.g. benzene, toluene, xylene, solvent naphtha and alkylnaphthalenes), halogenated hydrocarbons (e.g. dichloroethane, chloroform, carbon tetrachloride and chlorobenzene), esters (e.g. ethyl acetate, diisopropyl phthalate, dibutyl phthalate and dioctyl phthalate), amides (e.g. dimethylformamide, diethylformamide and dimethylacetamide), nitriles (e.g. acetonitrile), and dimethyl sulfoxide.

The following are typical examples of the adjuvant, which are used depending upon purposes and used alone or in combination is some cases, or need not be used at all.

To emulsify, disperse, dissolve and/or wet a compound as active ingredient, a surfactant is used. As the surfactant, there can be exemplified polyoxyethylene alkyl ethers, polyoxyethylene alkylaryl ethers, polyoxyethylene higher fatty acid esters, polyoxyethylene resonates, polyoxyethylene sorbitan monolaurate, polyoxyethylene sorbitan monooleate, alkylarylsulfonates, naphthalene sulfonic acid condensation products, ligninsulfonates and higher alcohol sulfate.

Further, to stabilize the dispersion of a compound as active ingredient, tackify it and/or bind it, the adjuvants exemplified below may also be used, namely, there may also be used adjuvants such as casein, gelatin, starch, methyl cellulose, carboxymethyl cellulose, gum arabic, poly(vinyl alcohol), turpentine, bran oil, bentonite and ligninsulfonates. To improve the flowability of a solid product, the following adjuvants may also be used, namely, there may be used adjuvants such as waxes, stearates, alkyl phosphates, etc.

Adjuvants such as naphthalenesulfonic acid condensation products and polycondensates of phosphates may be used as a peptizer for dispersible products, and adjuvants such as silicone oils may also be used as a defoaming agent. Adjuvants such as 1,2-benzisothiazoline-3-one, parachlorometaxylenol, butyl paraoxybenzoate may also be added as a preservative.

Further, if necessary, functional spreading agents, synergists such as metabolic inhibitor like piperonyl butoxide, anti-freezing agents such as propylene glycol, antioxidants such as BHT, ultraviolet absorbers, and the like may also be added.

The content of the compound as active ingredient may be varied as required, and the compound as active ingredient may be used in a proportion properly chosen in the range of 0.01 to 90 parts by weight per 100 parts by weight of the agricultural or horticultural insecticide. For example, in dusts, granules, emulsion or wettable powder, the suitable content of the compound as active ingredient is from 0.01 to 50% by weight.

The agricultural or horticultural insecticide of the present invention is used to control a variety of insect pests in the following manner: it is applied to a crop on which the insect pests are expected to appear, or a site where appearance or growth of the insect pests is undesirable, as it is or after being properly diluted with or suspended in water or the like, in an amount effective for control of the insect pests.

The applying dosage of the agricultural or horticultural insecticide of the present invention is varied depending upon various factors such as a purpose, insect pests to be controlled, a growth state of a plant, tendency of insect pests appearance, weather, environmental conditions, a preparation form, an application method, an application site and application time. It may be properly chosen in the range of 0.001 g to 10 kg, preferably 0.01 g to 1 kg, (in terms of the compound as active ingredient) per 10 ares depending upon purposes.

The agricultural or horticultural insecticide of the present invention may be used in admixture with other agricultural or horticultural insecticides, acaricides, nematocides, fungicides, biological agrochemicals or the like in order to expand both spectrum of controllable insect pest species and the period of time when effective application are possible or to reduce the dosage. Furthermore, the agricultural or horticultural insecticide of the present invention may be used in admixture with herbicides, plant-growth regulators, fertilizers or the like, depending upon application situations.

As the other agricultural or horticultural insecticides, acaricides and nematocides, which are used for the above purpose, there can be exemplified agricultural or horticultural insecticides, acaricides and nematocides, such as Ethion, Trichlorfon, Metamidophos, Acephate, Dichlorvos, Mevinphos, Monocrotophos, Malathion, Dimethoate, Formothion, Mecarbam, Vamidothion, Thiometon, Disulfoton, Oxydeprofos, Naled, Methylparathion, Fenitrothion, Cyanophos, Propaphos, Fenthion, Prothiofos, Profenofos, Isofenphos, Temephos, Phenthoate, Dimethylvinphos, Chlorfenvinphos, Tetrachlorvinphos, Phoxim, Isoxathion, Pyraclofos, Methidathion, Chlorpyrifos, Chlorpyrifos-methyl, Pyridaphenthion, Diazinon, Pirimiphosmethyl, Phosalone, Phosmet, Dioxabenzophos, Quinalphos, Terbuphos, Ethoprophos, Cadusafos, Mesulfenfos, DPS (NK-0795), Phosphocarb, Fenamiphos, Isoamidophos, Fosthiazate, Isazophos, Ethoprophos, Fenthion, Fostietane, Dichlofenthion, Thionazin, Sulprofos, Fensulfothion, Diamidafos, Pyrethrin, Allethrin, Prallethrin, Resmethrin, Permethrin, Tefluthrin, Bifenthrin, Fenpropathrin, Cypermethrin, α-Cypermethrin, Cyhalothrin, λ-Cyhalothrin, Deltamethrin, Acrinathrin, Fenvalerate, Esfenvalerate, Cycloprothrin, Ethofenprox, Halfenprox, Silafluofen, Flucythrinate, Fluvalinate, Methomyl, Oxamyl, Thiodicarb, Aldicarb, Alanycarb, Cartap, Metolcarb, Xylylcarb, Propoxur, Phenoxycarb, Fenobucarb, Ethiophencarb, Fenothiocarb, Bifenazate, Fenobucarb, Carbaryl, Pirimicarb, Carbofuran, Carbosulfan, Furathiocarb, Benfuracarb, Aldoxycarb, Diafenthiuron, Diflubenzuron, Teflubenzuron, Hexaflumuron, Novaluron, Lufenuron, Flufenoxuron, Chlorfluazuron, Fenbutatin oxide, tricyclohexyltin hydroxide, sodium oleate, potassium oleate, Methoprene, Hydroprene, Binapacryl, Amitraz, Dicofol, Kersen, Chrorobenzilate, Bromopropylate, Tetradifon, Bensultap, Benzoximate, Tebufenozide, Methoxyfenozide, pyridalyl, Chromafenozide, Propargite, Acequinosyl, Endosulfan, Diofenolan, Chlorfenapyl, Fenpyroximate, Tolfenpyrad, Fipronil, Tebufenpyrad, Triazamate, Etoxazole, Hexythiazox, nicotine sulfate, Nitenpyram, Acetamiprid, Thiacloprid, Imidacloprid, Thiamethoxam, Clothianidin, Dinotefuran, Fluazinam, Pyriproxyfen, Hydramethylnon, Pyrimidifen, Pyridaben, Cyromazin, TPIC (tripropyl isocyanurate), Pymetrozin, Clofentezin, Buprofedin, Thiocyclam, Fenazaquin, Chinomethionate, Indoxacarb, Polynactin complexes, Milbemectin, Abamectin, Emamectin-benzoate, Spinosad, BT (*Bacillus thuringiensis*), Azadirachtin, Rotenone, hydroxypropyl starch, Levamisole hydrochloride, Metam-sodium, Morantel tartrate, Dazomet, Trichlamide, Pasteuria, Monacrosporium-phymatophagum, etc.

As the agrohorticultural fungicides used for the same purpose as above, there can be exemplified agrohorticultural fungicides such as sulfur, lime sulfur, copper sulfate basic, Iprobenfos, Edifenfos, Tolclofos-methyl, Thiram, Polycarbamate, Zineb, Maneb, Mancozeb, Propineb, Thiophanate, Thiophanate methyl, Benomyl, Iminoctadin acetate, Iminocutadin albecylate, Mepronil, Flutolanil, Pencycuron, Furametpyl, Thifluzamide, Metalaxyl, Oxadixyl, Carpropamid, Dichlofluanid, Flusulfamide, Chlorothalonil, Kresoxim-methyl, Fenoxanil, Himexazol, Etridiazol, Fluoroimide, Procymidone, Vinclozolin, Iprodione, Triadimefon, Triflumizole, Bitertanol, Triflumizol, Ipconazole, Fluconazole, Propiconazole, Diphenoconazole, Myclobutanil, Tetraconazole, Hexaconazole, Tebuconazole, Imibenconazole, Prochloraz, Pefurazoate, Cyproconazole, Isoprothiolane, Fenarimol, Pyrimetanil, Mepanipyrim, Pyrifenox, Fluazinam, Triforine, Diclomezine, Azoxystrobin, Trifloxystrobin, Orysastrobin, Tiadiazin, Captan, Thiadinil, Probenazole, Acibenzolar-5-methyl (CGA-245704), Fthalide, Tricyclazole, Pyroquilon, Chinomethionat, Oxolinic acid, Dithianon, Cyazofamid, Tiadinil, Diclocymet, Kasugamycin, Validamycin, Polyoxin, Blasticidin, Streptomycin, etc.

Similarly, as the herbicides, there can be exemplified herbicides such as Glyphosate, Sulfosate, Glyfosinate, Bialaphos, Butamifos, Esprocarb, Prosulcarb, Benthiocarb, Pyributycarb, Asulam, Linulon, Dymron, Isouron, Bensulfuron methyl, Cyclosulfamuron, Cinosulfuron, Pyrazosulfuron ethyl, Azimsulfuron, Imazosulfuron, Tenylchlor, Alachlor, Pretilachlor, Clomeprop, Etobenzanid, Mefenacet, Flufenacet, Fentrazamide, Pendimethalin, Bifenox, Acifluorfen, Lactfen, Cyhalofop-butyl, Ioxynil, Bromobutide, Alloxydim, Setoxydim, Napropamide, Indanofan, Pyrazolate, Benzofenap, Pyraflufen-ethyl, Imazapyl, Sulfentrazone, Cafenstrole, Bentoxazon, Oxadiazon, Paraquat, Diquat, Pyriminobac, Simazine, Atrazine, Dimethametryn, Triazyflam, Benfuresate, Fluthiacet-methyl, Quizalofop-ethyl, Bentazone, Oxaziclomefone, Azafenidin, Benzobicyclon, calcium peroxide, etc.

As to the biological agrochemicals, the same effect as above can be expected by using the agricultural or horticultural insecticide of the present invention in admixture with, for example, viral formulations obtained from nuclear polyhedrosis virus (NPV), granulosis virus (GV), cytoplasmic polyhedrosis virus (CPV), entomopox virus (EPV), etc.; microbial insecticides utilized as insecticides or nematicides, such as *Monacrosporium phymatophagum, Steinernema carpocapsae, Steinernema kushidai, Pasteuria penetrans*, etc.; microbial insecticides utilized as fungicides, such as *Trichoderma lignorum, Agrobacterium radiobactor*, nonpathogenic *Erwinia carotovora, Bacillus subtilis*, etc.; and biological agrochemicals utilized as herbicides, such as *Xanthomonas campestris*, etc.

In addition, the agricultural or horticultural insecticide of the present invention can be used in combination with biological agrochemicals including natural enemies such as Parasitic wasp (*Encarsia formosa*), Parasitic wasp (*Aphidius colemani*), Gall-mildge (*Aphidoletes aphidimyza*), Parasitic wasp (*Diglyphus isaea*), Parasitic mite (*Dacnusa sibirica*), Predatory mite (*Phytoseiulus persimilis*), Predatory mite (*Amblyseius cucumeris*), Predatory bug (*Orius sauteri*), etc.; microbial insecticides such as *Beauveria brongniartii*, etc.; and pheromones such as (Z)-10-tetradecenyl acetate, (E,Z)-4,10-tetradecadienyl acetate, (Z)-8-dodecenyl acetate, (Z)-11-tetradecenyl acetate, (Z)-13-icosen-10-one, 14-methyl-1-octadecene, etc.

EXAMPLES

Representative Examples of the present invention are illustrated below, but the present invention is not limited to these.

Example 1

Production of $N^2$-(1,1-dimethyl-2-methylthioethyl)-3-iodo-$N^1$-[4-(5-n-heptafluoropropyltetrazol-1-yl)-2-methylphenyl]phthalamide (Compound No. 3-19)

(1-1) Production of 4-n-heptafluoropropylcarbonylamino-2-methylnitrobenzene

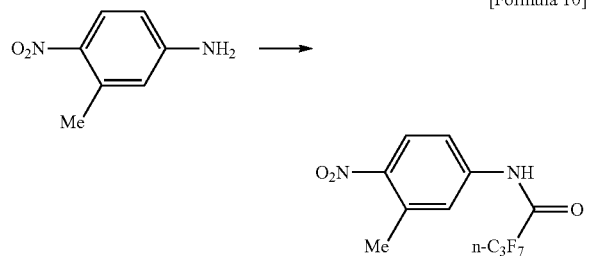

[Formula 10]

8.1 g (20 mmol) of anhydrous n-heptafluorobutric acid was added dropwise to a solution of 3.0 g (20 mmol) of 4-amino-2-methylnitrobenzene and 2.4 g (24 mmol) of triethylamine in 50 ml of tetrahydrofuran while cooled with water and ice. The reaction mixture was allowed to room temperature and after stirred for 12 hours, poured into iced water and the mixture was extracted with ethyl acetate. The organic layer was dried over anhydrous magnesium sulfate and then concentrated under reduced pressure to obtain 6.8 g of the desired compound.

Yield: quantitative

Physical properties: [$^1$HNMR, CDCl$_3$, δ (ppm)] 8.21 (br, 1H), 8.10 (d, 1H), 7.64 (d, 1H), 7.62 (dd, 1H), 2.68 (s, 3H).

(1-2) Production of 4-(5-n-heptafluoropropyltetrazol-1-yl)-2-methylnitrobenzene

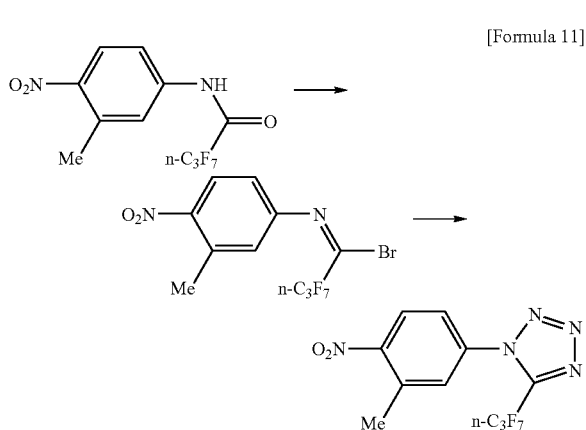

[Formula 11]

4.8 g (19 mmol) of triphenylphosphine and 6.1 g (19 mmol) of carbon tetrabromide were added to a solution of 4.3 g (12 mmol) of 4-n-heptafluoropropylcarbonylamino-2-methylnitrobenzene in 30 ml of acetonitrile and heated to reflux for three hours. The reaction mixture was concentrated under reduced pressure and then dissolved in 30 ml of DMF and slowly added dropwise in a DMF solution containing 2.4 g (37 mmol) of sodium azide. The reaction solution was stirred for five hours, poured into water and extracted with ethyl acetate. The organic layer was dried over anhydrous magnesium sulfate and concentrated under reduced pressure, and the residual substance was purified with silica gel column chromatography to obtain 2.5 g of the desired compound.

Yield: 34%

Physical properties: [$^1$HNMR, CDCl$_3$, δ (ppm)] 8.19 (d, 1H), 7.51 (s, 1H), 7.50 (d, 1H), 2.71 (s, 3H).

(1-3) Production of 4-(5-n-heptafluoropropyltetrazol-1-yl)-2-methyl-aniline (Compound No. 7-3)

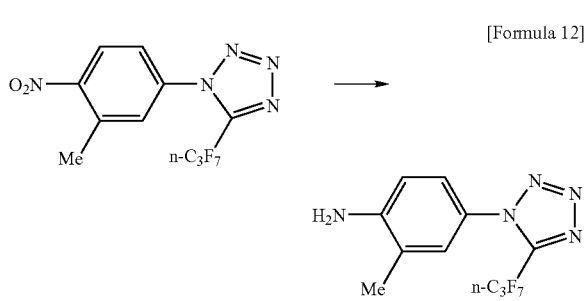

[Formula 12]

0.4 g of 5% palladium carbon was added to a solution of 2.5 g (6.7 mmol) of 4-(5-n-heptafluoropropyltetrazol-1-yl)-2-methylnitrobenzene in 70 ml of ethanol and the mixture was stirred under 3 atm hydrogen atmosphere overnight. The reaction mixture was filtered and concentrated under reduced pressure to obtain 2.1 g of the desired compound.

Yield: 85%

Physical properties: [$^1$HNMR, CDCl$_3$, δ (ppm)] 7.24 (m, 3H), 7.18 (m, 2H), 2.36 (s, 3H).

(1-4) Production of 3-iodo-N$^1$-[4-(5-n-heptafluoro-propyltetrazol-1-yl)-2-methylphenyl]-N$^2$-(1,1-dimethyl-2-methylthioethyl)phthalamide (Compound No. 3-19)

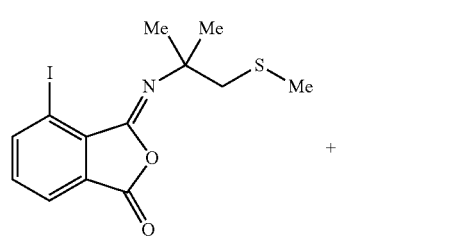

[Formula 13]

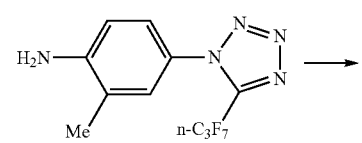

0.7 g (2.0 mmol) of 3-iodo-N-(1,1-dimethyl-2-methylthioethyl)phthalisoimide was dissolved in 10 ml of acetonitrile. 0.7 g (2.0 mmol) of 4-(5-n-heptafluoropropyltetrazol-1-yl)-2-methylaniline and 10 mg of trifluoroacetic acid were added thereto and the mixture was stirred at room temperature for 12 hours. Precipitated crystals were filtered and washed with acetonitrile to obtain 0.65 g of the desired compound.

Yield: 46%

Physical properties: Melting point 164-166° C.

Example 2

Production of 3-iodo-N$^1$-[4-(5-n-heptafluoropropyltetrazol-1-yl)-2-methylphenyl]-N$^2$-(1,1-dimethyl-2-methylsulfonylethyl)phthalamide (Compound No. 3-21)

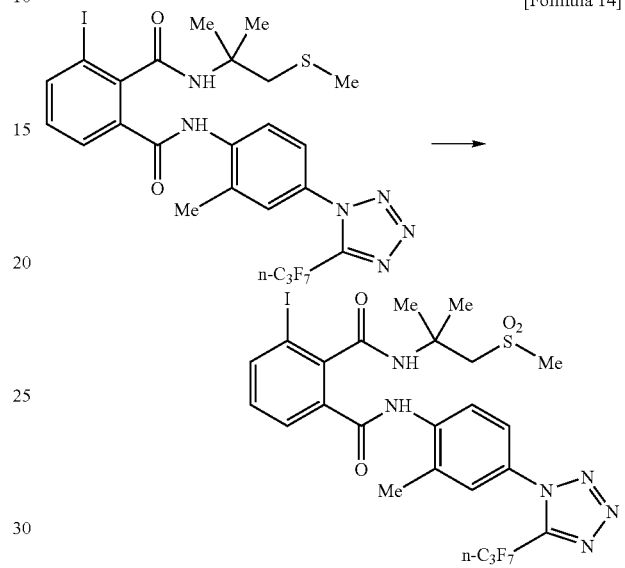

[Formula 14]

0.3 g (1.2 mmol) of m-chloroperbenzoic acid was added to a solution of 0.4 g (0.6 mmol) 3-iodo-N$^1$-[4-(5-n-heptafluoropropyl tetrazol-1-yl)-2-methylphenyl]-N$^2$-(1,1-dimethyl-2-methylthioethyl)phthalamide in 10 ml of chloroform while cooled with iced water and stirred under room temperature for three hours. A potassium carbonate aqueous solution and then a sodium sulfite aqueous solution were added thereto and the mixture was extracted with chloroform. The organic layer was dried over anhydrous magnesium sulfate and then concentrated under reduced pressure. The obtained crystals were washed with ether and to obtain 0.37 g of 3-iodo-N$^1$-[4-(5-n-heptafluoropropyltetrazol-1-yl)-2-methylphenyl]-N$^2$-(1,1-dimethyl-2-methylsulfonylethyl)phthalamide.

Yield: 93%

Physical properties: Melting point 141-142° C.

Example 3

Production of N$^2$-(1,1-dimethyl-2-methylthioethyl)-3-iodo-N$^1$-[4-(1-cyclopropyltetrazol-5-yl)-2-methylphenyl]phthalamide (Compound No. 4-1)

(3-1) Production of N-cyclopropyl-3-methyl-4-nitrobenzamide

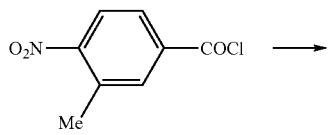

[Formula 15]

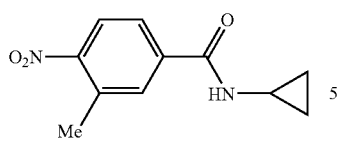

3.35 g (33 mmol) of triethylamine was added to a solution containing 1.65 g (29 mmol) of cyclopropylamine in 50 ml of tetrahydrofuran, then 5.0 g (28 mmol) of 3-methyl-4-nitrobenzoyl chloride was added dropwise while cooled with iced water. The reaction mixture was allowed to room temperature and after stirred for 12 hours, poured into iced water and the mixture was extracted with ethyl acetate. The organic layer was dried over anhydrous magnesium sulfate and then concentrated under reduced pressure to obtain 4.7 g of the desired compound. This was used in the next reaction without being purified.

(3-2) Production of 4-(1-cyclopropyltetrazol-5-yl)-2-methylnitrobenzene

[Formula 16]

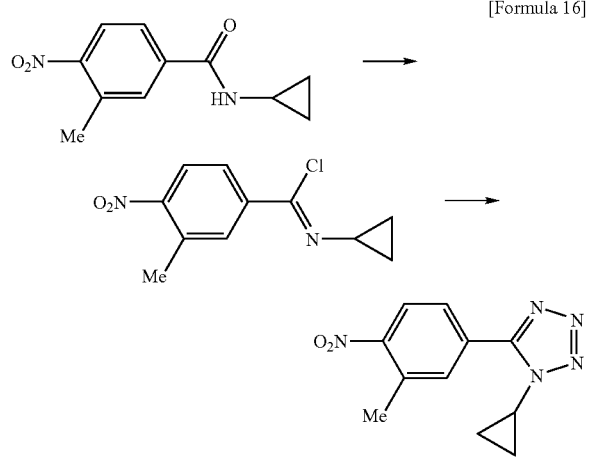

6.3 g (30 mmol) of phosphorus pentachloride was added to a mixture of 40 ml of toluene and 4 ml of dioxane containing 4.7 g (21 mmol) of N-cyclopropyl-3-methyl-4-nitrobenzamide and the mixture was heated to reflux for three hours. The reaction mixture was concentrated under reduced pressure, then dissolved in 30 ml of DMF and slowly added dropwise to a DMF solution containing 2.8 g (43 mmol) of sodium azide. The reaction mixture was stirred for five hours, then poured into water and extracted with ethyl acetate. The organic layer was dried over anhydrous magnesium sulfate and then concentrated under reduced pressure. The residue was filtered and washed with ether to obtain 3.7 g of the desired compound.

Yield: 71%

Physical properties: [$^1$HNMR, CDCl$_3$, δ (ppm)] 8.15 (d, 1H), 8.02 (s, 1H), 7.97 (d, 1H), 3.76 (m, 1H), 2.71 (s, 3H), 1.39 (m, 4H).

(3-3) Production of 4-(1-cyclopropyltetrazol-5-yl)-2-methylaniline (Compound No. 8-1)

[Formula 17]

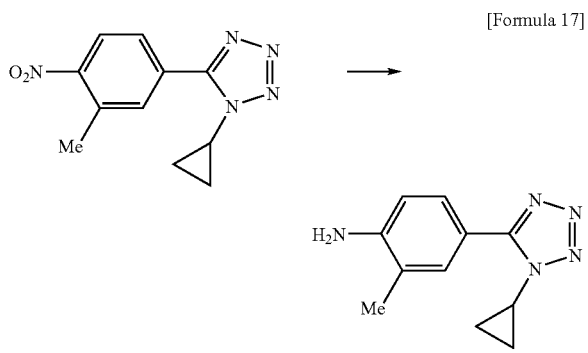

0.4 g of 5% palladium carbon was added to a solution of 1.6 g (6.5 mmol) of 4-(1-cyclopropyltetrazol-5-yl)-2-methylnitrobenzene in 70 ml of ethanol and the mixture was stirred under 3 atm hydrogen atmosphere overnight. The reaction mixture was filtered and concentrated under reduced pressure and the residual substance was purified with silica gel column chromatography to obtain 1.0 g of the desired compound.

Yield: 72%

Physical properties: Melting point 139-140° C.

(3-4) Production of N$^2$-(1,1-dimethyl-2-methylthio-ethyl)-3-iodo-N$^1$-[4-(1-cyclopropyltetrazol-5-yl)-2-methylphenyl]phthalamide (Compound No. 4-1)

[Formula 18]

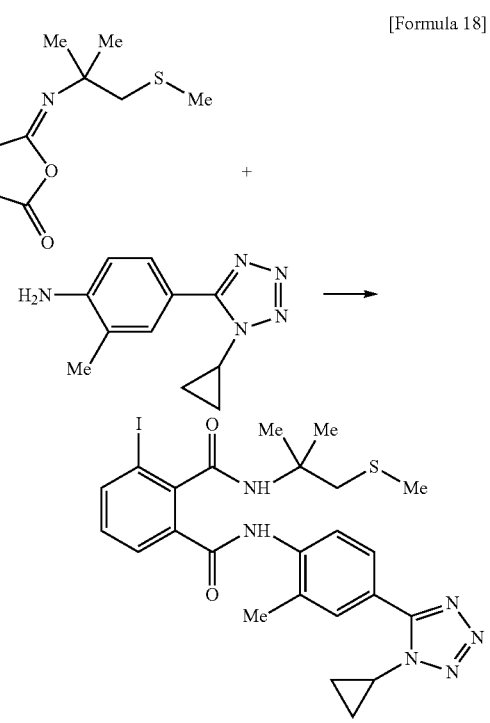

0.8 g (2.3 mmol) of 3-iodo-N-(1,1-dimethyl-2-methylthio-ethyl)phthalisoimide was dissolved in 10 ml of acetonitrile, 0.50 g (2.3 mmol) of 4-(1-cyclopropyltetrazol-5-yl)-2-methylaniline and 10 mg of trifluoroacetic acid were added thereto and the mixture was stirred at room temperature for 12 hours. Precipitated crystals were filtered and washed with acetonitrile to obtain 1.30 g of the desired compound.

Yield: 99%

Physical properties: Melting point 131-132° C.

Representative compounds of phthalamide of the present invention represented by general formula (I) that can be produced as in Examples are exemplified in Tables 1 to 4, and representative compounds of the aniline derivatives which are the intermediates thereof and represented by general formula (III) are exemplified in Tables 5 to 8 but the present invention is not limited to these.

Here in the Tables, "Me" represents a methyl group, "Et" represents an ethyl group, "Pr" represents a propyl group, "Ph" represents a phenyl group, and "c-" represents cyclo-. NMR data of the compounds for which physical properties are not described in Tables 5 to 8 are shown in Table 9.

TABLE 1

General formula (I-3)

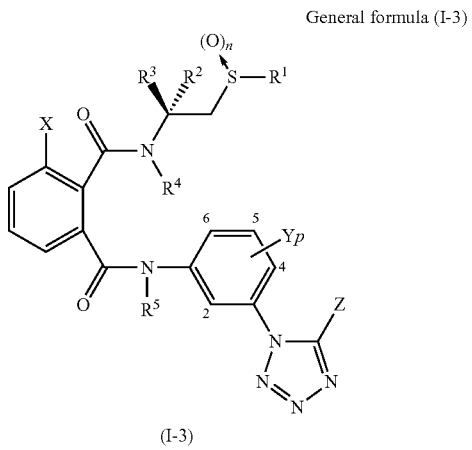

(I-3)

($R^1 = R^3$ = Me, $R^4 = R^5$ = H, Y$p$ = 2-Me)

| No. | X | $R^2$ | n | Z | Physical Properties Melting point (° C.) |
|---|---|---|---|---|---|
| 1-1 | I | H | 0 | $CF_3$ | |
| 1-2 | I | H | 1 | $CF_3$ | |
| 1-3 | I | H | 2 | $CF_3$ | |
| 1-4 | I | Me | 0 | $CF_3$ | 209-211 |
| 1-5 | I | Me | 1 | $CF_3$ | 113-117 |
| 1-6 | I | Me | 2 | $CF_3$ | 137-140 |
| 1-7 | I | H | 0 | $CF_2CF_3$ | |
| 1-8 | I | H | 1 | $CF_2CF_3$ | |
| 1-9 | I | H | 2 | $CF_2CF_3$ | |
| 1-10 | I | Me | 0 | $CF_2CF_3$ | |
| 1-11 | I | Me | 1 | $CF_2CF_3$ | |
| 1-12 | I | Me | 2 | $CF_2CF_3$ | |
| 1-13 | I | H | 0 | $CF_2CF_2CF_3$ | 85-99 |
| 1-14 | I | H | 1 | $CF_2CF_2CF_3$ | |
| 1-15 | I | H | 2 | $CF_2CF_2CF_3$ | 104-110 |
| 1-16 | I | Me | 0 | $CF_2CF_2CF_3$ | 184-186 |
| 1-17 | I | Me | 1 | $CF_2CF_2CF_3$ | 102-106 |
| 1-18 | I | Me | 2 | $CF_2CF_2CF_3$ | 114-118 |
| 1-19 | I | Me | 0 | 3-$CF_3$Ph | 109-112 |
| 1-20 | I | Me | 1 | 3-$CF_3$Ph | |
| 1-21 | I | Me | 2 | 3-$CF_3$Ph | 110-116 |

TABLE 2

General formula (I-4)

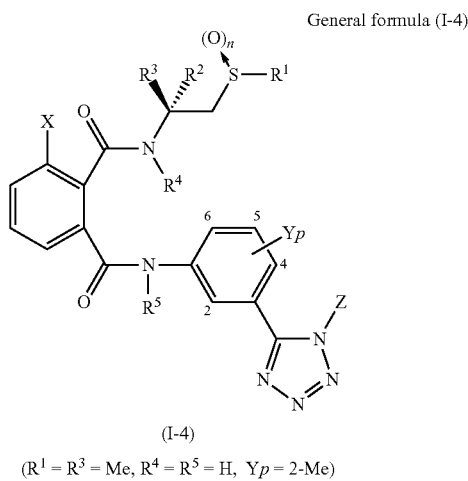

(I-4)

($R^1 = R^3$ = Me, $R^4 = R^5$ = H, Y$p$ = 2-Me)

| No. | X | $R^2$ | n | Z | Physical properties Melting point (° C.) |
|---|---|---|---|---|---|
| 2-1 | I | Me | 0 | 2-$CF_3$Ph | |
| 2-2 | I | Me | 1 | 2-$CF_3$Ph | |
| 2-3 | I | Me | 2 | 2-$CF_3$Ph | |
| 2-4 | I | H | 0 | 3-$CF_3$Ph | 234-236 |
| 2-5 | I | H | 1 | 3-$CF_3$Ph | |
| 2-6 | I | H | 2 | 3-$CF_3$Ph | 99-109 |
| 2-7 | I | Me | 0 | 3-$CF_3$Ph | 191-192 |
| 2-8 | I | Me | 1 | 3-$CF_3$Ph | |
| 2-9 | I | Me | 2 | 3-$CF_3$Ph | 99-106 |
| 2-10 | I | Me | 0 | 4-$CF_3$Ph | 110-111 |
| 2-11 | I | Me | 1 | 4-$CF_3$Ph | |
| 2-12 | I | Me | 2 | 4-$CF_3$Ph | 115-118 |
| 2-13 | I | H | 0 | 3,5-$(CF_3)_2$Ph | 220-221 |
| 2-14 | I | H | 1 | 3,5-$(CF_3)_2$Ph | |
| 2-15 | I | H | 2 | 3,5-$(CF_3)_2$Ph | 194-196 |
| 2-16 | I | Me | 0 | 3,5-$(CF_3)_2$Ph | 192-194 |
| 2-17 | I | Me | 1 | 3,5-$(CF_3)_2$Ph | |
| 2-18 | I | Me | 2 | 3,5-$(CF_3)_2$Ph | 149-152 |

TABLE 3

General formula (I-5)

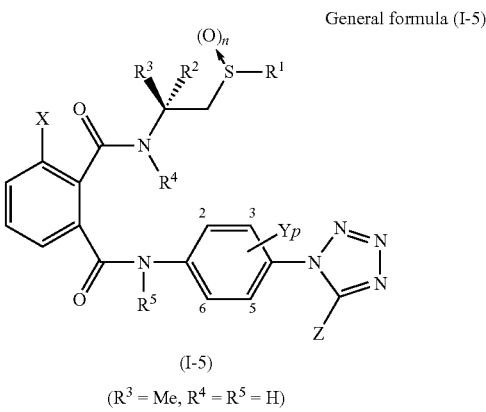

(I-5)

($R^3$ = Me, $R^4 = R^5$ = H)

| No. | X | $R^1$ | $R^2$ | n | Yp | Z | Physical properties Melting point (° C.) |
|---|---|---|---|---|---|---|---|
| 3-1 | I | Me | Me | 0 | 2-Me | c-Pr | 150-152 |
| 3-2 | I | Me | Me | 1 | 2-Me | c-Pr | |
| 3-3 | I | Me | Me | 2 | 2-Me | c-Pr | 118-121 |
| 3-4 | I | Me | H | 0 | 2-Me | $CF_3$ | |

TABLE 3-continued

General formula (I-5)

(I-5)

($R^3$ = Me, $R^4$ = $R^5$ = H)

| No. | X | $R^1$ | $R^2$ | n | Yp | Z | Physical properties Melting point (° C.) |
|---|---|---|---|---|---|---|---|
| 3-5 | I | Me | H | 1 | 2-Me | $CF_3$ | |
| 3-6 | I | Me | H | 2 | 2-Me | $CF_3$ | |
| 3-7 | I | Me | Me | 0 | 2-Me | $CF_3$ | 173-175 |
| 3-8 | I | Me | Me | 1 | 2-Me | $CF_3$ | 105-110 |
| 3-9 | I | Me | Me | 2 | 2-Me | $CF_3$ | 103-112 |
| 3-10 | I | Me | H | 0 | 2-Me | $CF_2CF_3$ | |
| 3-11 | I | Me | H | 1 | 2-Me | $CF_2CF_3$ | |
| 3-12 | I | Me | H | 2 | 2-Me | $CF_2CF_3$ | |
| 3-13 | I | Me | Me | 0 | 2-Me | $CF_2CF_3$ | 154-156 |
| 3-14 | I | Me | Me | 1 | 2-Me | $CF_2CF_3$ | 68-72 |
| 3-15 | I | Me | Me | 2 | 2-Me | $CF_2CF_3$ | 99-106 |
| 3-16 | I | Me | H | 0 | 2-Me | $CF_2CF_2CF_3$ | 106-112 |
| 3-17 | I | Me | H | 1 | 2-Me | $CF_2CF_2CF_3$ | |
| 3-18 | I | Me | H | 2 | 2-Me | $CF_2CF_2CF_3$ | 127-129 |
| 3-19 | I | Me | Me | 0 | 2-Me | $CF_2CF_2CF_3$ | 164-166 |
| 3-20 | I | Me | Me | 1 | 2-Me | $CF_2CF_2CF_3$ | 128-133 |
| 3-21 | I | Me | Me | 2 | 2-Me | $CF_2CF_2CF_3$ | 141-142 |
| 3-22 | Cl | Me | H | 0 | 2-Me | $CF_2CF_2CF_3$ | 84-88 |
| 3-23 | Cl | Me | H | 1 | 2-Me | $CF_2CF_2CF_3$ | |
| 3-24 | Cl | Me | H | 2 | 2-Me | $CF_2CF_2CF_3$ | 110-114 |
| 3-25 | I | Me | Me | 0 | 2-Cl | $CF_2CF_2CF_3$ | 125-127 |
| 3-26 | I | Me | Me | 1 | 2-Cl | $CF_2CF_2CF_3$ | |
| 3-27 | I | Me | Me | 2 | 2-Cl | $CF_2CF_2CF_3$ | 123-126 |
| 3-28 | I | Me | H | 0 | 2-Me | $CF_2CF_2CF_2CF_3$ | 170-172 |
| 3-29 | I | Me | H | 1 | 2-Me | $CF_2CF_2CF_2CF_3$ | |
| 3-30 | I | Me | H | 2 | 2-Me | $CF_2CF_2CF_2CF_3$ | 108-112 |
| 3-31 | I | Me | Me | 0 | 2-Me | $CF_2CF_2CF_2CF_3$ | 157-158 |
| 3-32 | I | Me | Me | 1 | 2-Me | $CF_2CF_2CF_2CF_3$ | 109-111 |
| 3-33 | I | Me | Me | 2 | 2-Me | $CF_2CF_2CF_2CF_3$ | 89-93 |
| 3-34 | Cl | Me | H | 0 | 2-Me | $CF_2CF_2CF_2CF_3$ | 183-184 |
| 3-35 | Cl | Me | H | 1 | 2-Me | $CF_2CF_2CF_2CF_3$ | |
| 3-36 | Cl | Me | H | 2 | 2-Me | $CF_2CF_2CF_2CF_3$ | 108-110 |
| 3-37 | I | Et | H | 0 | 2-Me | $CF_2CF_2CF_2CF_3$ | 172-174 |
| 3-38 | I | Et | H | 1 | 2-Me | $CF_2CF_2CF_2CF_3$ | |
| 3-39 | I | Et | H | 2 | 2-Me | $CF_2CF_2CF_2CF_3$ | 92-101 |
| 3-40 | I | Me | H | 0 | 2-Me | $CF_2CF_2CF_2CF_2CF_3$ | |
| 3-41 | I | Me | H | 1 | 2-Me | $CF_2CF_2CF_2CF_2CF_3$ | |
| 3-42 | I | Me | H | 2 | 2-Me | $CF_2CF_2CF_2CF_2CF_3$ | |
| 3-43 | I | Me | H | 0 | 2-Me | $CF_2CF_2CF_2CF_2CF_2CF_3$ | |
| 3-44 | I | Me | H | 1 | 2-Me | $CF_2CF_2CF_2CF_2CF_2CF_3$ | |
| 3-45 | I | Me | H | 2 | 2-Me | $CF_2CF_2CF_2CF_2CF_2CF_3$ | |
| 3-46 | I | Me | H | 0 | 2-Me | $CF_2CHF_2$ | |
| 3-47 | I | Me | H | 1 | 2-Me | $CF_2CHF_2$ | |
| 3-48 | I | Me | H | 2 | 2-Me | $CF_2CHF_2$ | |
| 3-49 | I | Me | H | 0 | 2-Me | $CF_2CF_2CHF_2$ | |
| 3-50 | I | Me | H | 1 | 2-Me | $CF_2CF_2CHF_2$ | |
| 3-51 | I | Me | H | 2 | 2-Me | $CF_2CF_2CHF_2$ | |
| 3-52 | I | Me | H | 0 | 2-Me | $CF_2CF_2CF_2CHF_2$ | |
| 3-53 | I | Me | H | 1 | 2-Me | $CF_2CF_2CF_2CHF_2$ | |
| 3-54 | I | Me | H | 2 | 2-Me | $CF_2CF_2CF_2CHF_2$ | |
| 3-55 | I | Me | H | 0 | 2-Me | $CF_2CF_2CF_2CF_2CHF_2$ | 151-153 |
| 3-56 | I | Me | H | 1 | 2-Me | $CF_2CF_2CF_2CF_2CHF_2$ | |
| 3-57 | I | Me | H | 2 | 2-Me | $CF_2CF_2CF_2CF_2CHF_2$ | 98-106 |
| 3-58 | Cl | Me | H | 0 | 2-Me | $CF_2CF_2CF_2CF_2CHF_2$ | 153-154 |
| 3-59 | Cl | Me | H | 1 | 2-Me | $CF_2CF_2CF_2CF_2CF_2CHF_2$ | |
| 3-60 | Cl | Me | H | 2 | 2-Me | $CF_2CF_2CF_2CF_2CF_2CHF_2$ | 92-98 |
| 3-61 | I | Me | H | 0 | 2-Me | $CH(CF_3)_2$ | |
| 3-62 | I | Me | H | 1 | 2-Me | $CH(CF_3)_2$ | |
| 3-63 | I | Me | H | 2 | 2-Me | $CH(CF_3)_2$ | |
| 3-64 | I | Me | Me | 0 | 2-Me | 2-$CF_3$Ph | 218-219 |
| 3-65 | I | Me | Me | 1 | 2-Me | 2-$CF_3$Ph | |
| 3-66 | I | Me | Me | 2 | 2-Me | 2-$CF_3$Ph | 201-203 |

TABLE 4

General formula (I-6)

(I-6)

($R^1$ = $R^3$ = Me, $R^4$ = $R^5$ = H, Yp = 2-Me)

| No. | X | $R^2$ | n | Z | Physical properties Melting point (° C.) |
|---|---|---|---|---|---|
| 4-1 | I | Me | 0 | c-Pr | 131-132 |
| 4-2 | I | Me | 1 | c-Pr | |
| 4-3 | I | Me | 2 | c-Pr | 90-97 |
| 4-4 | I | Me | 0 | $CF_3CH_2$ | 164-165 |
| 4-5 | I | Me | 1 | $CF_3CH_2$ | 84-90 |
| 4-6 | I | Me | 2 | $CF_3CH_2$ | 98-102 |
| 4-7 | I | Me | 0 | 3,5-$(CF_3)_2$Ph | 138-139 |
| 4-8 | I | Me | 1 | 3,5-$(CF_3)_2$Ph | |
| 4-9 | I | Me | 2 | 3,5-$(CF_3)_2$Ph | 115-117 |

TABLE 5

General formula (III-5)

(III-5)

| No. | Z | Physical properties |
|---|---|---|
| 5-1 | $CF_3$ | 162-164 |
| 5-2 | $CF_3CF_2$ | |
| 5-3 | $CF_3CF_2CF_2$ | NMR |
| 5-4 | 3-$CF_3$Ph | 93-94 |

TABLE 6

General formula (III-6)

(III-6)

| No. | Z | Physical properties |
|---|---|---|
| 6-1 | 2-$CF_3$Ph | |
| 6-2 | 3-$CF_3$Ph | 107-109 |
| 6-3 | 4-$CF_3$Ph | 151-153 |
| 6-4 | 3,5-$(CF_3)_2$Ph | 124-126 |

TABLE 7

General formula (III-7)

(III-7)

| No. | Y | Z | Physical properties |
|---|---|---|---|
| 7-1 | Me | $CF_3$ | 82-84 |
| 7-2 | Me | $CF_2CF_3$ | 88-90 |
| 7-3 | Me | $CF_2CF_2CF_3$ | NMR |
| 7-4 | H | $CF_2CF_2CF_3$ | 98-100 |
| 7-5 | Cl | $CF_2CF_2CF_3$ | 66-68 |
| 7-6 | Me | $CF_2CF_2CF_2CF_3$ | 100-102 |
| 7-7 | Me | $CF_2CF_2CF_2CF_2CF_3$ | |
| 7-8 | Me | $(CF_2)_6CF_3$ | |
| 7-9 | Me | $(CF_2)_6CF_3$ | |
| 7-10 | Me | $(CF_2)_7CF_3$ | |
| 7-11 | Me | $(CF_2)_8CF_3$ | |
| 7-12 | Me | $(CF_2)_9CF_3$ | |
| 7-13 | Me | $CF_2CHF_2$ | |
| 7-14 | Me | $CF_2CF_2CHF_2$ | |
| 7-15 | Me | $CF_2CF_2CF_2CHF_2$ | |
| 7-16 | Me | $(CF_2)_5CHF_2$ | 87-89 |
| 7-17 | Me | $(CF_2)_7CHF_2$ | |
| 7-18 | Me | $(CF_2)_9CHF_2$ | |
| 7-19 | Me | $CF(CF_3)_2$ | |

TABLE 7-continued

General formula (III-7)

(III-7)

| No. | Y | Z | Physical properties |
|---|---|---|---|
| 7-20 | Me | $CH(CF_3)_2$ | |
| 7-21 | Me | c-Pr | 95-97 |
| 7-22 | Me | 2-$CF_3$Ph | 128-131 |

TABLE 8

General formula (III-8)

(III-8)

| No. | Z | Physical properties |
|---|---|---|
| 8-1 | c-Pr | 139-140 |
| 8-2 | $CF_3CH_2$ | 85-86 |
| 8-3 | 3,5-$(CF_3)_2$Ph | 169-170 |

TABLE 9

| No. | $^1$H-NMR[CDCl$_3$/TMS, δ-value(ppm)] |
|---|---|
| 5-3 | 7.21 (m, 1H), 7.18 (m, 2H), 4.30 (br, 2H), 2.36 (s, 3H) |
| 7-3 | 7.24 (m, 3H), 7.18 (m, 2H), 2.36 (s, 3H) |

Hereinbelow, representative formulation examples and test examples of the present invention are shown but the present invention is not limited to these.

In the formulation examples, "part(s)" means part(s) by weight.

Formulation Example 1

| | |
|---|---|
| Compounds described in Tables 1 to 4 | 10 parts |
| Xylene | 70 parts |
| N-methylpyrrolidone | 10 parts |
| Mixture of polyoxyethylene nonylphenyl ether with calcium alkylbenzene sulfonate | 10 parts |

The above materials are uniformly mixed and dissolved to prepare an emulsion preparation.

Formulation Example 2

| | |
|---|---|
| Compounds described in Tables 1 to 4 | 3 parts |
| Clay powder | 82 parts |
| Diatomous earth powder | 15 parts |

The above materials are uniformly mixed and pulverized to prepare a powder preparation.

Formulation Example 3

| Compounds described in Tables 1 to 4 | 5 parts |
|---|---|
| Mixed powder of bentonite and clay | 90 parts |
| Calcium lignosulfonate | 5 parts |

The above materials are uniformly mixed, kneaded with an appropriate amount of water and granulated and dried to prepare a granular preparation.

Formulation Example 4

| Compounds described in Tables 1 to 4 | 20 parts |
|---|---|
| Kaolin and synthetic high dispersion silicic acid | 75 parts |
| Mixture of polyoxyethylene nonylphenyl ether with calcium alkylbenzenesulfonate | 5 parts |

The above materials are uniformly mixed and pulverized to prepare a wettable preparation.

1. Test Example

Insecticidal Test on Diamondback Moth (*Plutella xylostella*)

Adult diamondback moths were left for breeding on Chinese cabbage seedlings and allowed to lay eggs. Two days after the start of breeding, the Chinese cabbage seedlings with the deposited eggs were dipped in drug solution for about 30 seconds in which a drug containing a compound described in Tables 1 to 4 as an active ingredient was diluted to 50 ppm, and allowed to stand still in a temperature-controlled chamber at 25° C. after air-dried. Six days after dipping in a drug solution, the number of hatched insects was counted. Insect mortality was calculated by the following formula and estimation was conducted according to the following criteria. 1 Lot, 10 insects, 3 series system.

[Expression 1]

$$\text{Insect mortality (\%)} = \frac{\text{Number of hatched insects in non-treated lot} - \text{Number of hatched insects in treated lot}}{\text{Number of hatched insects in non-treated lot}} \times 100$$

Criteria
A . . . Insect mortality 100%
B . . . Insect mortality 99%-90%
C . . . Insect mortality 89%-80%
D . . . Insect mortality 79%-50%

As a result of the above test, Compounds which showed the A-rank insecticidal activity were found to be 1-4, 1-5, 1-6, 1-13, 1-15, 1-16, 1-17, 1-18, 1-19, 1-21, 2-4, 2-6, 2-7, 2-10, 2-1.2, 2-13, 2-15, 2-16, 2-18, 3-7, 3-8, 3-9, 3-13, 3-14, 3-15, 3-16, 3-18, 3-19, 3-20, 3-21, 3-22, 3-24, 3-25, 3-27, 3-28, 3-30, 3-31, 3-32, 3-33, 3-34, 3-36, 3-37, 3-39, 3-55, 3-57, 3-58, 3-60, 4-4, 4-5, 4-7, 4-9.

Test Example 2

Insecticidal Test on *Spodoptera litura*

Cabbage leaves (variety: Shikikaku) were dipped in a drug solution for about 30 seconds in which a drug containing a compound described in Tables 1 to 4 as an active ingredient was diluted to 500 ppm, and placed in plastic dishes of 9 cm in diameter after air-dried. Second-instar lava of *Spodoptera litura* were inoculated and then the dishes were covered with a lid and allowed to stand in a temperature-controlled chamber at 25° C. Eight days after the inoculation, the number of living or dead insects was counted. Insect mortality was calculated by the following formula and estimation was conducted according to the same criteria as in Test Example 1. 1 Lot, 10 insects, 3 series system.

[Expression 2]

$$\text{Insect mortality (\%)} = \frac{\text{Number of living insect in non-treated lot} - \text{Number of living insect in treated lot}}{\text{Number of living insect in non-treated lot}} \times 100$$

As a result of the above test, Compounds which showed the A-rank insecticidal activity were found to be 1-4, 1-5, 1-6, 1-13, 1-15, 1-16, 1-17, 1-18, 1-19, 1-21, 2-7, 2-10, 2-12, 2-13, 2-15, 3-7, 3-8, 3-9, 3-13, 3-14, 3-15, 3-16, 3-18, 3-19, 3-20, 3-21, 3-22, 3-24, 3-25, 3-27, 3-28, 3-30, 3-31, 3-32, 3-33, 3-34, 3-36, 3-37, 3-39, 3-55, 3-57, 3-58, 3-60, 4-7.

Test Example 3

Insecticidal Test on Smaller Tea Tortrix (*Adoxophyes* sp.)

Tea leaves were dipped in a drug solution for about 30 seconds in which a drug containing a compound described in Tables 1 to 4 as an active ingredient was diluted to 500 ppm, and placed in plastic dishes of 9 cm in diameter after air-dried. Smaller tea tortrix lava were inoculated and then the dishes were allowed to stand in a temperature-controlled chamber at 25° C. at a humidity of 70%. Eight days after the inoculation, the number of living or dead insects was counted. Insect mortality was calculated by the following formula and estimation was conducted according to the same criteria as in Test Example 2. 1 Lot, 10 insects, 3 series system.

As a result of the above test, Compounds which showed the A-rank insecticidal activity were found to be 1-4, 1-13, 1-15, 1-16, 1-17, 1-18, 2-7, 2-9, 2-13, 2-15, 2-18, 3-7, 3-8, 3-9, 3-13, 3-14, 3-18, 3-19, 3-20, 3-21, 3-22, 3-24, 3-25, 3-27, 3-28, 3-31, 3-32, 3-33, 3-34, 3-39, 3-55, 3-57, 3-58, 3-60, 4-7, 4-9.

The invention claimed is:

1. A phthalamide derivative shown by formula (I):

[Formula 1]

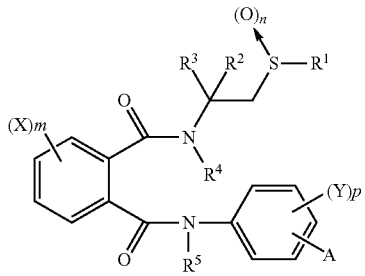

(I)

wherein $R^1$ is a $C_1$-$C_6$ alkyl group, a halo $C_1$-$C_6$ alkyl group, a $C_2$-$C_6$ alkenyl group, a halo $C_2$-$C_6$ alkenyl group, a $C_2$-$C_6$ alkynyl group or a halo $C_2$-$C_6$ alkynyl group;

$R^2$ and $R^3$ may be the same or different, and each is a hydrogen atom, a $C_1$-$C_6$ alkyl group, a halo $C_1$-$C_6$ alkyl group, a $C_2$-$C_6$ alkenyl group, a halo $C_2$-$C_6$ alkenyl group, a $C_2$-$C_6$ alkynyl group or a halo $C_2$-$C_6$ alkynyl group;

$R^4$ and $R^5$ may be the same or different, and each is a hydrogen atom, a $C_1$-$C_6$ alkyl group, a $C_2$-$C_6$ alkenyl group, a $C_2$-$C_6$ alkynyl group, a $C_1$-$C_6$ alkylcarbonyl group, a halo $C_1$-$C_6$ alkylcarbonyl group, a $C_1$-$C_6$ alkoxycarbonyl group or a halo $C_1$-$C_6$ alkoxycarbonyl group;

A is a tetrazolyl group shown by A-1

[Formula 2]

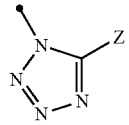

(A-1)

wherein Z is a halo $C_1$-$C_{10}$ alkyl group;
or A-2

[Formula 3]

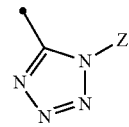

(A-2)

wherein Z is the same as above;

X is a halogen atom, a nitro group, a cyano group, a $C_1$-$C_6$ alkyl group, a halo $C_1$-$C_6$ alkyl group, a $C_1$-$C_6$ alkoxy group, a halo $C_1$-$C_6$ alkoxy group, a $C_1$-$C_6$ alkylthio group, a halo $C_1$-$C_6$ alkylthio group, a $C_1$-$C_6$ alkylsulfinyl group, a halo $C_1$-$C_6$ alkylsulfinyl group, a $C_1$-$C_6$ alkylsulfonyl group or a halo $C_1$-$C_6$ alkylsulfonyl group, and m is an integer of from 0 to 4;

Y is a halogen atom, a nitro group, a cyano group, a $C_1$-$C_6$ alkyl group, a halo $C_1$-$C_6$ alkyl group, a $C_1$-$C_6$ alkoxy group, a halo $C_1$-$C_6$ alkoxy group, a $C_1$-$C_6$ alkylthio group, a halo $C_1$-$C_6$ alkylthio group, a $C_1$-$C_6$ alkylsulfinyl group, a halo $C_1$-$C_6$ alkylsulfinyl group, a $C_1$-$C_6$ alkylsulfonyl group or a halo $C_1$-$C_6$ alkylsulfonyl group, and p is an integer of from 0 to 4;

n is an integer of from 0 to 2; or a salt thereof.

2. The phthalamide derivative or a salt thereof according to claim 1, wherein $R^1$ is a $C_1$-$C_6$ alkyl group, $R^2$ and $R^3$, which may be the same or different, each is a hydrogen atom, a $C_1$-$C_6$ alkyl group or a halo $C_1$-$C_6$ alkyl group, $R^4$ and $R^5$ each is a hydrogen atom, A is A-1 or A-2, Z is a halo $C_1$-$C_{10}$ alkyl group, X is a halogen atom or a $C_1$-$C_6$ halo alkyl group, m is 1 or 2, Y is a halogen atom, a $C_1$-$C_6$ alkyl group or a halo $C_1$-$C_6$ alkyl group, and p is an integer of from 0 to 2 and n is an integer of from 0 to 2.

3. The phthalamide derivative or the salt thereof according to claim 1, wherein $R^1$ is a $C_1$-$C_6$ alkyl group, $R^2$ and $R^3$, which may be the same or different, each is a hydrogen atom or a $C_1$-$C_6$ alkyl group, $R^4$ and $R^5$ each is a hydrogen atom, A is A-1 or A-2, Z is a halo $C_1$-$C_{10}$ alkyl group, X is a halogen atom, m is 1, Y is a halogen atom or a $C_1$-$C_6$ alkyl group, p is 1, and n is an integer of from 0 to 2.

* * * * *